(12) United States Patent
Vandier et al.

(10) Patent No.: US 9,161,944 B2
(45) Date of Patent: Oct. 20, 2015

(54) METHOD FOR PREVENTING CANCER METASTASIS

(75) Inventors: Christophe Vandier, Tours (FR); Philippe Bougnoux, Tours (FR); Aurelle Chantome, Tours (FR); Bernard Corbel, Brest (FR); Alban Girault, Tours (FR); Jean-Pierre Haelters, Brest (FR); Virginie Joulin, Villejuif (FR); Marie Potier-Cartereau, Tours (FR); Gaelle Simon, Brest (FR)

(73) Assignees: INSERM (INSTITUT NATIONAL DE LA SANTE ET DE LA SANTE ET DE LA RECHERCHE MEDICALE), Paris (FR); UNIVERSITE DE BRETAGNE OCCIDENTALE (U.B.O.), Brest (FR); UNIVERSITE FRANCOIS-RABELAIS DE TOURS, Tours (FR)

( * ) Notice: Subject to any disclaimer, the term of this patent is extended or adjusted under 35 U.S.C. 154(b) by 6 days.

(21) Appl. No.: 13/577,734

(22) PCT Filed: Feb. 17, 2011

(86) PCT No.: PCT/EP2011/052351

§ 371 (c)(1),
(2), (4) Date: Oct. 15, 2012

(87) PCT Pub. No.: WO2011/101408

PCT Pub. Date: Aug. 25, 2011

(65) Prior Publication Data

US 2013/0029925 A1    Jan. 31, 2013

(30) Foreign Application Priority Data

Feb. 18, 2010    (EP) ..................................... 10305169

(51) Int. Cl.
| | |
|---|---|
| *A61K 31/7028* | (2006.01) |
| *A61K 31/7008* | (2006.01) |
| *A61K 31/7016* | (2006.01) |
| *A61K 31/7004* | (2006.01) |
| *A61K 31/702* | (2006.01) |
| *C07H 11/04* | (2006.01) |
| *C07H 15/04* | (2006.01) |

(52) U.S. Cl.
CPC ........... *A61K 31/7028* (2013.01); *A61K 31/702* (2013.01); *A61K 31/7004* (2013.01); *A61K 31/7008* (2013.01); *A61K 31/7016* (2013.01); *C07H 11/04* (2013.01); *C07H 15/04* (2013.01)

(58) Field of Classification Search
None
See application file for complete search history.

(56) References Cited

U.S. PATENT DOCUMENTS

| | | |
|---|---|---|
| 5,385,685 A | 1/1995 | Humphreys et al. |
| 6,153,736 A | 11/2000 | Bittman et al. |
| 6,245,754 B1 | 6/2001 | Kozikowski et al. |

FOREIGN PATENT DOCUMENTS

| | | |
|---|---|---|
| CN | 1850762 | 10/2006 |
| DE | 19634021 | 2/1998 |
| WO | 02/060911 | 8/2002 |
| WO | 2004/062586 | 7/2004 |
| WO | 2009/092170 | 7/2009 |

OTHER PUBLICATIONS

Germanov, E., Berman, J. N., & Guernsey, D. L. (2006). Current and future approaches for the therapeutic targeting of metastasis (Review). International journal of molecular medicine, 18(6), 1025.*
Maeda, N., Kokai, Y., Ohtani, S., Sahara, H., Kumamoto-Yonezawa, Y., Kuriyama, I., . . . & Mizushina, Y. (2008). Anti-tumor effect of orally administered spinach glycolipid fraction on implanted cancer cells, colon-26, in mice. Lipids, 43(8), 741-748.*
Malisan, F., & Testi, R. (2002). GD3 ganglioside and apoptosis. Biochimica et Biophysica Acta (BBA)-Molecular and Cell Biology of Lipids, 1585(2), 179-187.*
Danker, K., Reutter, W., & Semini, G. (2010). Glycosidated phospholipids: uncoupling of signalling pathways at the plasma membrane. British journal of pharmacology, 160(1), 36-47.*
Simon, P. M. (1994). Complex carbohydrates in development as human pharmaceuticals. Exp. Opin. Invest. Drugs, 3(3), 223-239.*
Database WPI Section Ch, Week 200729 Oct. 25, 2006, Thomson Scientific, London, GB; AN 2007-293235 XP002583382, Liu et al., "Cyclic derivative keratinous sponge alcohol, and its preparing method and use".
Guivisdalsky et al., "Synthesis and antineoplastic properties of ether-linked Thioglycolipids," J. Med. Chem., 33:2614-2621 (1990).
International Search Report in PCT/EP2011/052351, dated May 23, 2011.
Kuriyama et al., "Inhibitory effects of glycolipis fraction from spinach on mammalian DNA polymerase activity and human cancer cell proliferation," J. Nutritional Biochem., 16(10):594-601 (2005) XP005081588.
Rinker-Schaeffer CV: "Metastasis Suppressor proteins: Discovery, Molecular Mechanisms, and Clinical Appplication", Clinical Cancer Research, vol, 12, No. 13, Jul. 1, 2006, pp. 3882-3889, XP055115795.
Sava G et al.: "Drug control of solid tumour metastases : a critical view.";, Anticancer Research, vol. 19, No. 2A, Mar. 1999, pp. 1117-1124, XP0091778814.
Potier M et al. : "Identification of SK3 channel as a new mediator of breast cancer cell migration", Molecular Cancer Therapeutics, vol. 5, No. 11, Nov. 1, 2006, pp. 2946-2953, XP002428454.
Chantome et al.: "KCa2.3 channel-dependent hyperpolarization increases melanoma cell mobility", Experimental Cell Research, vol. 315, No. 20, Dec. 10, 2009, pp. 3620-3630, XP026766770.

\* cited by examiner

*Primary Examiner* — Eric Olson
*Assistant Examiner* — Dale R Miller
(74) *Attorney, Agent, or Firm* — McAndrews, Held & Malloy Ltd.

(57) ABSTRACT

The present invention relates to the use of a specific family of glycerolipid compounds of formula (I) described in the detailed description or the manufacture of a medicament for the prevention or for the treatment of cancer metastasis.

7 Claims, 19 Drawing Sheets

JPH1701

METHOD FOR PREVENTING CANCER METASTASIS

The present application is filed pursuant to 35 U.S.C. 371 as a U.S. National Phase application of International Patent Application No. PCT/EP2011/052351, which was filed Feb. 17, 2011, claiming the benefit of priority to European Patent Application No. 10305169.4, which was filed on Feb. 18, 2010. The entire text of the aforementioned applications is incorporated herein by reference in its entirety.

FIELD OF THE INVENTION

The present invention relates to the medical field, and more especially to the prevention and to the treatment of cancer metastasis.

BACKGROUND OF THE INVENTION

Anti-cancer compounds that are already known or commercially marketed exert their anti-cancer properties through various ways, including through direct action on cancer cells. A number of the anti-cancer agents that act directly on cancer cells block cancer cell proliferation or are cytotoxic for cancer cells.

However, even after complete removal or treatment of a primary cancer, a malignant tumour often metastasizes. A metastatic malignant tumour is formed at a location distant from the primary lesion as a result of the metastasis of the primary tumor. This is one of the most important concerns in cancer therapy. Specifically, even if a primary lesion is treated, a patient may die because of the growth of a tumor that has metastasized to another organ. In the case of many types of clinically diagnosed solid cancer (a type of tumor that is a primary lesion resulting from the local growth of cancer), surgical obliteration is thought to be the first means for treatment. However, primary cancer cell metastasis is often observed after surgical operation. Cancer infiltration at a metastatic site spreads over the whole body, so that the patient will die due to the growth of metastatic cancer. It has been reported that for individual bodies having resectable tumors, primary tumor growth or local recurrence are often causes of death. It is thus currently considered that almost 40% of cancer victims with operable tumors will finally die because of metastatic disease following surgical operation.

Accordingly, malignant tumor metastasis is the most common reason for failed cancer therapies (see Bertino et al., (edited in 1996), Encyclopedia of Cancer, Academic Press; Devita et al., (edited in 1997), Cancer: Principles & Practice of Oncology, Lippincott, Williams and Wilkins; Cavalli et al., (1996), Textbook of Medical Oncology, Dunitz Martin Ltd; Peckham et al., (edited in 1995), Oxford Textbook of Oncology, Oxford Univ. Press; and Mendelsohn et al., (1995), The Molecular Basis of Cancer, Saunders, Philadelphia).

Malignant melanoma, breast cancer, lung cancer, colon cancer, and prostate cancer are thought to be cancer types that tend to metastasize. The range of metastasis differs depending on a cancer type. The lungs and the liver are well known as target organs of cancer, and the brain or the bone marrow is also a target organ at a high frequency. Bone metastasis differs from metastasis to other organs, such that it rarely directly threatens life. However, bone metastasis is complicated by excruciating bone ache, the restriction of physical activity, or the like, thereby significantly lowering patient quality of life (QOL) and indirectly causing one's early death.

Metastasis is a very complex process resulting of various genetic or epigenetic mutations and each stage of metastasis is believed to be regulated by specific intracellular signal transduction pathways. Invasion mechanisms initiate the metastatic process and consist of changes in tumour cells adherence to cells and to the extracellular matrix, proteolytic degradation of surrounding tissue and motility to physically proper a tumor cell through tissue, all those steps are specifically regulated by signal transduction pathways.

The multi-step process of metastasis includes, (i) release of malignant cells from the primary neoplasm, (ii) migration of cancer cells into circulation, (iii) adhesion at distant sites, and (iv) growth of the disseminated cancer cells within the vessels or within the tissue following extravasation. Each step in this process requires different types of interaction between cancer cells and the host microenvironment.

While the details of the mechanisms by which metastasis occurs and thus may be inhibited have not been fully elucidated yet, it is however obvious that the biological mechanisms involved in the transformation of a non-cancer cell to a cancer cell are clearly distinct from the mechanisms involved in the generation of cancer cell metastasis (Steeg P S, Nat. Medicine 2006, vol. 12, (8), 895-904). For example recent works establish a clear distinction between several cellular pathways leading to cancer cell proliferation and metastatic invasion mechanisms (McLean, G. et al., Nat. Rev. Cancer 5, 505-514 (2005); Playford, M. & Schaller, M., Oncogene 23, 7928-7946 (2004); Birchmeier, C et al., Nat. Rev. Mol. Cell. Biol. 4, 915-925 (2003)).

Moreover, while identification of specific metastasis genes is difficult because of the need for several complementary functions that might be fulfilled by different genes in different contexts, more than 20 metastasis suppressors have currently been identified. Metastasis suppressors act by different mechanisms than tumor suppressors, and have no effect on primary tumors. These genes inhibit metastases without blocking tumour formation (Rinker-Schaeffer C W et al., Clin Cancer Res 2006; 12:3882-89; Berger J C et al., Cancer Biol Ther 2005; 4:805-12; Nash K T et al., Front Biosci 2006; 11:647-59; Shevde L A et al., Cancer Lett 2003; 198:1-20; Steeg P S et al., Clin Breast Cancer 2003; 4:51-62).

It has therefore became obvious that if the targeting of the proliferation and/or apoptosis mechanisms may be needed in order to eliminate the primary tumour, it is necessary, in order to achieve a complete remission, to differentially address metastatic processes.

Indeed, although anti-cancer agents, including those having anti-proliferative activity against cancer cells, have proved therapeutic efficiency against primary tumors, almost none of these anti-cancer agents possess concomitantly anti-metastasis activity.

Preclinical studies indeed report differential effects of drugs on primary and metastatic disease. These data illustrate that compounds validated on the reduction of the size of primary tumor may not work on metastatic disease. On the contrary, anti-metastatic efficacy may not be validated in tests based on the reduction of primary tumor size (Steeg P S, Nature Medicine, 12 (8), 895-905 (2006); Lang, J. Y. et al. Clin. Cancer Res. 11, 3455-3464 (2005); Shannon, K. E. et al. Clin. Exp. Metastasis 21, 129-138 (2004); Manni, A. et al. Clin. Exp. Metastasis 20, 321-325 (2003); Cairns, R. A. & Hill, R. P. Cancer Res. 64, 2054-2061 (2004); Lovey, J. et al., Strahlenther. Onkol. 179, 812-818 (2003); Nasulewicz, A. et al. Biochim. Biophys. Acta 1739, 26-32 (2004)).

Furthermore, other studies have shown that chemotherapeutics targeting the primary tumor can alter metastatic properties. For example, in vitro treatment of nasal carcinoma cell line with melphalan has been shown to increase its invasiveness (Liang, Y. et al. Eur. J. Cancer 37, 1041-1052 (2001)).

The mechanisms responsible for the effect on metastasis are unknown and may be multifactorial. There are at least the following two possibilities: (a) that the treatment is accelerating mutation and exerting a selective pressure that encourages the outgrowth of more aggressive cellular variants or (b) that the stress associated with the treatment is inducing epigenetic changes such as alterations in gene expression that enhance the ability of cells to form viable metastases (Cairns R. A. & Hill R. P. Cancer Res., 64, 2054-61 (2004)).

Therefore regarding the development of anti-metastatic drugs, the most interesting target are the molecules of the cellular processes which control the metastatic spread without interfering with the primary tumour growth.

In the last 20 years, some teams have dedicated themselves to find "true" (i.e.: specifically targeting metastatic processes) antimetastatic drugs. Some of those anti-metastatic drugs, such as razoxane, inhibit intravasation of metastatic cells by elaborating a physical barrier, which does not limit the growth of the primary tumour (Bergamo et al., Dalton trans., 2007, 13, 1267-1272). Most of them inhibit different steps of colonization (Perret & Crepin, Fundamental and Clinical Pharmacology, 2008, 22, 465-92).

Previous works which have shown a direct relationship between the ability of cancer cells to migrate in vitro and their capacity to metastasize in vivo, have also opened possibilities to identify new anti-metastatic targets (see notably Giamperi et al., 2009, Nature Cell Biology, Vol. 11(11): 1287-1296; Patent Application no US 2003/0054985, Hazan et al., 2000, The Journal of Cell biology, Vol. 148(4): 779-790; Yang et al., 2009, Cancer Cell, Vol. 15: 124-134).

A compound that has been the subject matter of promising experimental testing, including preliminary clinical trial phases, is the alkylglycerophospholipid compound named edelfosine (ET-18-OCH$_3$) (Vogler et al., Cancer Invest, 1998, 16(8):549-53, Candal et al., Cancer Chemother Pharmacol, 1994, 34(2), 175-8).

However, while edelfosine has been described in the art to possess anti-angiogenic and possibly anti-invasive effects, a clear understanding of his molecular action is lacking. For example it has been shown that edelfosine exerts a biphasic effect on angiogenesis depending on the dose (Vogler et al., Cancer Invest, 1998, 16(8):549-53, Candal et al., Cancer Chemother Pharmacol, 1994, 34(2), 175-8, Cajate C & Mollinedo F, Current Drug metabolism, 2002, 3, 491-525). Moreover, other closely related glycerolipids, such as PAF (Andrade S P et al., Int. J. Exp. Pathol., 1992, 73, 503-13) or butyryl-glycerol (Dobson D E, et al., Cell, 1990, 61, 223-30) have been reported to be pro-angiogenic.

Moreover, Edelfosine is not a "true" anti-metastatic drug, since it also targets the primary tumor growth and exerts pro-apoptotic effects (Gajate C and Mollinedo F, Curr. Drug Metab. 3, 491-525; Nieto-Miguel et al., 2007, Cancer Res, 67 (31); Estella-Hermoso de Mendoza et al., 2009, Clin Cancer Res, 15(3), 858-864).

Lastly, edelfosine is well known to be highly toxic when it is administered to human and its clinical therapeutic use was notably hampered by major adverse side effects (Gajate C and Mollinedo F, Curr. Drug Metab. 3, 491-525).

There is thus still a need in the art for methods for inhibiting tumor metastasis, and in particular for methods which inhibit metastasis without causing serious side effects to the treated cancer patient.

SUMMARY OF THE INVENTION

The present invention relates to the use of a glycerolipid of formula (I)

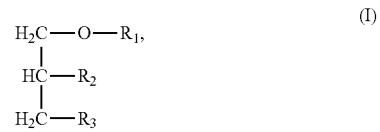

wherein:
$R_1$ is an alkyl or an alkenyl group having from 16 to 18 carbon atoms,
$R_2$ is a group selected from the group consisting of:
(a) a group of formula (II):

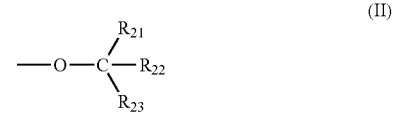

wherein $R_{21}$, $R_{22}$ and $R_{23}$, one independently from each other, are selected from the group consisting of hydrogen atom and an alkyl group having 1 or 2 carbon atoms, and
(b) a hydroxyl,
and
$R_3$ is selected from the group consisting of:
a monosaccharide group or a polysaccharide group having from 2 to 4 saccharide units, or
a group of formula (III)

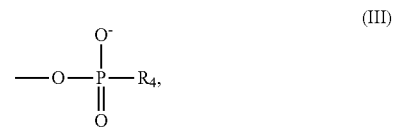

wherein $R_4$ is selected from the group consisting of a monosaccharide group or a
polysaccharide group having from 2 to 4 saccharide units, for manufacturing a medicament for preventing cancer metastasis.

This invention also relates to the use of a glycerolipid of formula (I) for preventing cancer metastasis.

This invention also pertains to a method for preventing cancer metastasis comprising a step of administering to a patient in need thereof a glycerolipid of formula (I) as described above.

A glycerolipid of formula (I) encompasses the compounds of formula (A) to (P) as detailed in the general description of the invention herein.

This invention also concerns a pharmaceutical composition for preventing cancer metastasis comprising a compound of formula (I) as defined above in combination with one or more pharmaceutically acceptable excipients.

Finally, the present invention pertains to a glycerolipid of formula (I) above per se.

DESCRIPTION OF THE FIGURES

FIG. 6: JPH1701 (or Ohmline) activity on cell motility on cancerous MDA-MB-435s cells and on non cancerous MCF-10A cells. The motility was tested by transwell assay. Additionally, viability tests were performed using MTT assays. FIG. 6E shows that the motility of MDA-MB-435s shRD=SK3+ cells expressing SK3 is affected by JPH1701 (the concentrations of JPH1701 are 0 (control condition), 10 nM, 100 nM, 300 nM and 1 µM). In contrast, as shown in FIG. 6F, JPH1701 does not affect the migration ability of MDA-MB-435s shSK3 which does not express SK3, excepted at 1 µM where it is shown a non-specific effect of JPH1701 (the concentrations of JPH1701 are 0 (control condition), 10 nM, 100 nM, 300 nM and 1 µM).

FIG. 7: Effects of a 24 hours application of JPH1701 at 1 µM on whole cell current in MDA-MB-435s Wild Type (WT).

FIG. 8: Effect of JPH1701 on SK3 channel activity.

FIG. 9. Selectivity effect of JPH1701 on SKCa subtype and on IKCa channels.

FIG. 10. Anti-metastatic effect of JPH1701 on experimental metastasis model. Two millions of MDA-MB-435s-luc cells pre-treated for 24 hours with JPH1701 (1 µM) or vehicle were grafted in MFP of NMRI/Nude mice. Mice were treated three times a week with JPH1701 at 15 mg/kg in i.v. or with vehicle during all the experiments (14-15 weeks). The primary tumor was surgical removed when its volume attempted 500 mm3 (6-7 weeks post-graft). Mice were euthanized 7-8 weeks after surgical removed of the primary tumor.

FIG. 11: Effects of JPH1701 on PAF receptor, PLC and PKCs activities.

FIG. 12: JPH1701 treatment did not affect the primary tumor growth in mammary fat pad (MFP)-model tumor. Two millions of MDA-MB-435s-luc cells pre-treated for 24 hours with JPH1701 (1 µM) or vehicle were grafted in MFP of NMRI/Nude mice. Mice were treated three times a week with JPH1701 at 15 mg/kg in i.v. or with vehicle.

DETAILED DESCRIPTION OF THE INVENTION

Figure 1:
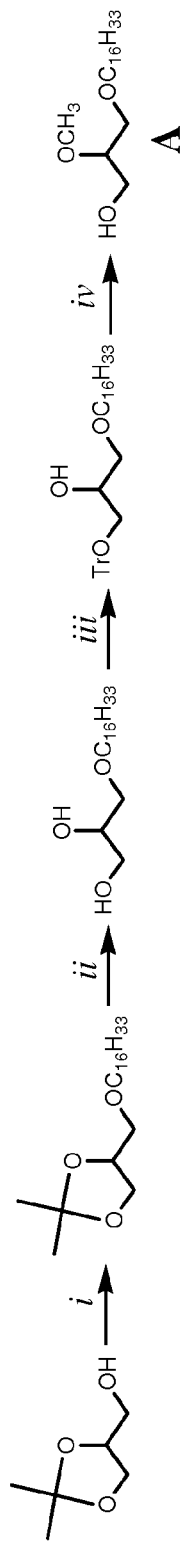
FIG. 1 illustrates a scheme of synthesis of the intermediate compound A that is a glycerol-lipid precursor useful for obtaining a compound of formula (I), and especially a compound of formula (I) wherein group $R_3$ denotes a monosaccharide or a polysaccharide group. This scheme is termed "scheme 1" in the present specification.

Surprisingly, it has been found according to the invention that a specific family of glycerolipid compounds, having the formula (I) described hereunder, possess specific anti-metastatic properties at least against tumor cells expressing the SK3/KCa2.3 channel Thus, this invention relates to the use of a glycerolipid of formula (I)

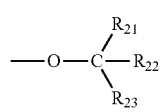
(I)

wherein:
$R_1$ is an alkyl or an alkenyl group having from 16 to 18 carbon atoms,
$R_2$ is a group selected from the group consisting of:
(a) a group of formula (II):

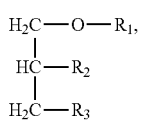
(II)

wherein $R_{21}$, $R_{22}$ and $R_{23}$, one independently from each other, are selected from the group consisting of hydrogen atom and an alkyl group having 1 or 2 carbon atoms, and
(b) a hydroxyl,
and
$R_3$ is selected from the group consisting of:
a monosaccharide group or a polysaccharide group having from 2 to 4 saccharide units, or a group of formula (III)

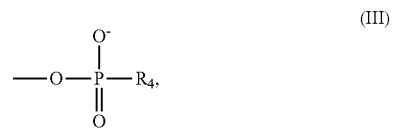
(III)

wherein $R_4$ is selected from the group consisting of a monosaccharide group or a
polysaccharide group having from 2 to 4 saccharide units, for manufacturing a medicament for preventing cancer metastasis.

Also, the present invention pertains to the use of a glycerolipid of formula (I) above for preventing cancer metastasis.

This invention also encompasses methods for preventing metastasis in a cancer patient in need thereof comprising a step of administering to the said patient a glyceroplid of formula (I) above, or a pharmaceutical composition comprising the said glycerolipid of formula (I) above. According to the invention, preventing metastasis encompasses impairing the spread of cells from the primary tumour to distant locations.

It has been found according to the invention that the compounds of formula (I) inhibit the activity of the SK3/KCa2.3 potassium channel and that the said inhibitory activity on the SK3/KCa2.3 channel contributes or even fully explains their anti-metastatic properties.

More precisely it has been found that compounds of formula (I), having a fatty acid length of at least 16 carbons in sn-1 ($R_1$) and a disaccharide in sn-3 ($R_3$) was strongly effective. Hexadecyloxy-2-O-methyl-sn-glycerol (HMG) analogues having a fatty acid length of at least 16 carbons in sn-1 ($R_1$) and where $R_3$ (sn-3) consists of:

and wherein $R_4$ is selected from the group consisting of a monosaccharide group or a polysaccharide group having from 2 to 4 saccharide units (compounds M, N, O and P for example) have also been demonstrated as potent inhibitors of SK3/KCa2.3 channels.

To determine whether SK3/KCa2.3 channel was essential in the cancer cell migration inhibitory effect of the compounds of formula (I), SK3/KCa2.3 mRNA were knocked down by transfecting cells with two sets of siRNA of SK3/KCa2.3 gene or with scrambled siRNA as negative control in MDA-MB-435s cell line, according to methods already disclosed in the European patent application no EP 1 884 774 published on Feb. 6, 2008 in the name of INSERM (Institut National de la Santé et de la Recherche Medicale).

The same confirmation that SK3/KCa2.3 channel was essential in the cancer cell migration inhibitory effect of the compounds of formula (I) was brought following infection of SK3/KCa2.3-expressing cancer cells with a lentivirus containing a shRNA directed against SK3/KCa2.3 mRNA.

Firstly, it was found that knocking-down SK3/KCa2.3 channel reduced the number of MDA-MB-435s migrating cells. Further, it was importantly found that knocking-down SK3/KCa2.3 channel totally suppressed the inhibitory effect of the compounds of formula (I) according to the invention on cell migration.

Still further, it has been found that SK3/KCa2.3-negative human cells that have been subsequently transfected with human SK3/KCa2.3 cDNA became sensitive to the inhibitory effect of the compounds of formula (I) according to the invention. Notably, it has been found that the compounds of formula (I) inhibit migration of cells transfected with SK3/KCa2.3 cDNA, whereas migration of the same SK3/KCa2.3-negative cells before transfection with SK3/KCa2.3 cDNA was not inhibited by the compounds of formula (I).

It has also been found that the compounds of formula (I) above were able to selectively target those metastasizing cancerous cells which are undergoing migration from the primary tumor site.

It has further been found that a glycerolipid of formula (I) has anti-metastatic effects in vivo.

These in vivo experimental results shown in the examples herein fully confirm previous works according to which there exists a direct relationship between the ability of a substance to inhibit in vitro migration of cancer cells and the ability of the same substance to behave in vivo as an anti-metastatic agent.

As it is shown in the examples herein, glycerolipids of formula (I) are of a high therapeutic interest in general for preventing metastasis in cancer patients.

A further important property of the glycerolipids of formula (I) consists of their low cytotoxicity, which means that the administration of these glycerolipids to cancer patients will not cause undesirable toxicity to the said patient. Indeed, it is shown that, at amounts of a glycerolipid of formula (I) that are effective for inhibiting cancer metastasis in vivo, the said glycerolipid of formula (I) causes no in vivo adverse effect.

It has additionally been demonstrated that a glycerolipid of formula (I) is a "true" anti-metastatic drug since it has no effect on the primary tumor growth. The results of the examples herein clearly show that a glycerolipid of formula (I), when it is administered in vivo in an animal model of cancer metastasis is (i) not toxic, (ii) anti-metastatic and (iii) has no effect on the primary tumor growth. This specificity will probably lead to a better tolerance as compared to non specific compounds. Targeting the cellular processes that control metastatic spread may also be a promising remission consolidation strategy, especially in cases where the primary tumor burden can be removed by surgery. Specificity and non toxicity are highly valuable properties of glycerolipids of formula (I) since, as it is known by the one skilled in the art, cancer patients are already weakened both by the disease and the general anti-cancer therapies against the primary tumors, and these patients are highly sensitive to the adverse effects that may be caused by any additional preventive or therapeutic treatment, including any additional treatment aimed at preventing or treating the occurrence of metastasis.

Notably, it has been shown in the examples herein that the compounds of formula (I) possess a far lower cytotoxic activity towards both cancerous and non-cancerous cells, as compared to structurally-related known cancer agents, including structurally close known cancer agents like edelfosine that have both anti-apoptotic and anti-metastatic effects.

Illustratively, edelfosine has been shown herein to exhibit an $IC_{50}$ of less than 5 µM after a 24 hour-incubation time in vitro with metastatic cancerous cell lines, whereas the compounds of formula (I) all possess an $IC_{50}$ of more than 10 µM towards the same metastatic cancerous cells. A number of the compounds of formula (I) that have been assayed for in vitro cytotoxicity exhibit an $IC_{50}$ of more than 50 µM, with a number of them which exhibit an $IC_{50}$ of more than 100 µM.

As used herein, the expression "low cytotoxicity" denotes that the compound of interest exhibits an $IC_{50}$ of more than 10 µM after a 24 hours time period of incubation of the test compound with target cells, when measured in an in vitro viability assay. Conventional in vitro cell viability assays that may be employed include (i) trypan blue assay and (ii) MTT assay. For assessing the "cytotoxicity" value of a compound for the purpose of the present invention, the MTT assay is preferably used as the reference assay.

Consequently, the glycerolipids of formula (I) consist of low cytotoxicity anti-metastatic agents. As intended herein, as a low cytotoxicity compound, a glycerolipid of formula (I) has an $IC_{50}$ value of more than 10 µM. An $IC_{50}$ value of more than 10 µM encompasses an $IC_{50}$ value of more than 11 µM, 12 µM, 13 µM, 14 µM, 15 µM, 16 µM, 17 µM, 18 µM, 19 µM, 20 µM, 21 µM, 22 µM, 23 µM, 24 µM, 25 µM, 26 µM, 27 µM, 28 µM, 29 µM, 30 µM, 31 µM, 32 µM, 33 µM, 34 µM, 35 µM, 36 µM, 37 µM, 38 µM, 39 µM, 40 µM, 41 µM, 42 µM, 43 µM, 44 µM, 45 µM, 46 µM, 47 µM, 48 µM, 49 µM, 50 µM, 51 µM, 52 µM, 53 µM, 54 µM, 55 µM, 56 µM, 57 µM, 58 µM, 59 µM, 60 µM, 61 µM, 62 µM, 63 µM, 64 µM, 65 µM, 66 µM, 67 µM, 68 µM, 69 µM, 70 µM, 71 µM, 72 µM, 73 µM, 74 µM, 75 µM, 76 µM, 77 µM, 78 µM, 79 µM, 80 µM, 81 µM, 82 µM, 83 µM, 84 µM, 85V, 86 µM, 87V, 88 µM, 89 µM, 90 µM, 91 µM, 92 µM, 93 µM, 94 µM, 95 µM, 96 µM, 97 µM, 98 µM, 99 µM and 100 µM, or more than 100 µM.

Illustratively, for assessing cytotoxicity of a given compound, the MTT assay may be performed using, as the main reagents, (1) a MTT solution wherein MTT is dissolved in Dulbecco's Modified Eagle Medium with 5% of foetal bovin serum at a final concentration of 0.5 mg/ml. Into the cells, MTT is transformed into formazan crystal which will be dissolved with pure Dimethylsulfoxyde. Briefly, the MTT assay may comprise the following steps:
   (a) seeding the target cells in a 24 well plate at the appropriate cell number, e.g. at a defined cell number per well (40000 cells par well) and leaving control wells without cells (used as control for minimum absorbance),
   (b) incubating the plate overnight at 37° C. in a humidified incubator, 5% $CO_2$,
   (c) adding the test compound to plate and including replicates for a range of concentrations. Include negative controls (including vehicle control) and a positive control (e.g. distilled water).
   (d) incubating the plate for the desired time period at 37° C. in a humidified incubator, 5% CO2,
   (e) adding the MTT reagent, e.g. 800 µl per well of the 24 well plate,
   (f) incubating at 37° C. for the desired time period following the cell lines, e.g. 45 minutes for MDA-MB-435s,
   (g) adding 1 volume (e.g 800 µl) of dimethylsulfoxyde,
   (h) after one hour incubation, pipetting each well to ensure dissolution of formazan precipitate,
   (i) determining the absorbance value for each well of the 96 well plate using 490 nm as test wavelength and 630 nm as the reference wavelength, and
   (j) determining the percentage of cell viability in each well with the following formula:

$$\% \text{ Viability} = \frac{\text{Mean Absorbance of Sample}}{\text{Mean Absorbance of Control}} \times 100$$

The MTT assay may also be performed by the one skilled in the art as disclosed by Roger et al. (2004, Biochim Biophys Acta, Vol. 1667: 190-199).

At the end of the cytotoxicity assay, the $IC_{50}$ value is determined as the half maximal (50%) inhibitory concentration (IC) of a substance tested.

Preferably, step (a) above is performed by using $4 \times 10^5$ target cells per well.

Preferably, step (a) is performed using human mestastazing cancerous cells, either primary culture cells or a cell line. More preferably, target cells consist of cell from metastasizing human breast cancer cells. Most preferably, as a reliable reference, target cells consist of cells from the MDA-MB-435s cell line (ATCC no HTB-129).

As already specified previously herein, compounds of formula (I) are useful as active ingredients for preventing the occurrence of metastasis in cancer patients, since it has been found herein that these compounds inhibit metastasizing cancerous cell migration in an in vitro cell migration assay.

Interestingly, it is shown in the examples herein that a glycerolipid of formula (I) has the ability of inhibiting metastasis formation in a wide variety of tissues and organs, including ovary, uterus, kidney, liver, lung, members (e.g. legs, arms), spinal column, spleen and lymph nodes. These latter results support the effectiveness of a glycerolipid of formula (I) as a general anti-metastatic agent, irrespective of the body localization of the metastasis focuses that are expected or that have already occurred. These latter results also support the effectiveness of a glycerolipid of formula (I), irrespective of the kind of cancer in which the occurrence of metastasis is to be prevented.

It has been found herein that the compounds of formula (I) inhibit 50% or more cell migration at a final concentration of 10 nM to 300 nM in the cell culture, depending of the compound of formula (I) that is assayed.

For assaying the inhibitory activity of a compound of formula (I), the one skilled in the art may refer to the assay disclosed by Roger et al. (2004, Biochim Biophys Acta, Vol. 1667: 190-199), which may be briefly described as a method comprising the steps of:
(a) bringing into contact metastasizing cancerous cells with a membrane possessing pores having an appropriate diameter for preventing non-migrating cells to cross the said membrane while allowing the migrating cells to cross the said membrane, and
(b) quantifying the cells that pass through the membrane.

For determining the inhibitory activity of a compound of formula (I), step (a) of the cell migration assay above is performed with cells that have previously been incubated with the said compound, at defined final concentrations in the culture medium. At the end of the assay, the number of cells incubated with compound (I) that have passed through the membrane is determined and is compared to the number of cells incubated with control culture medium that have passed the membrane, so as to calculate the percentage of inhibition of cell migration that is induced by the compound (I).

Alternatively, the cell migration inhibitory activity of a compound of formula (I) may be assessed by performing a Wound Healing assay that is disclosed in the examples herein and for which the one skilled in the art may also refer to the article of Rodriguez et al. (2005, Methods Biol Mol, Vol. 294: 23-29). The wound-healing assay is simple, inexpensive, and one of the earliest developed methods to study directional cell migration in vitro. This method mimics cell migration during wound healing in vivo. The basic steps involve creating a "wound" in a cell monolayer, capturing the images at the beginning and at regular intervals during cell migration to close the wound, and comparing the images to quantify the migration rate of the cells. It is particularly suitable for studies on the effects of cell-matrix and cell-cell interactions on cell migration. Cells are seeded in culture dishes and grown until confluence in DMEM supplemented with 10% foetal calf serum. The monolayer is then scratched with a sterile yellow pipette tip. Then, migration of cells to the cleared area is inspected under a microscope. Pictures are taken directly at the time of scratching and after 24 h, so as to determine the ability of the tested cells to migrate. The Wound Healing Assay is the migration assay that has been used in the examples herein to determine the ability of compounds of formula (I) to inhibit migration of metastatic cancer cells. The Wound Healing assay thus consists of the most preferred cell migration assay of reference according to the present invention.

In the examples herein, the said in vitro cell migration assay has been performed with human metastasizing cancerous cell line, namely the MDA-MB-435s cell line (ATCC no HTB-129).

As used herein, "a" or "an" may mean one or more. As used herein, when used in conjunction with the word "comprising", the words "a" or "an" may mean one or more than one. As used herein, "another" may mean at least a second or more.

As used herein, "alkyl" refers to a group of carbon and hydrogen atoms derived from an alkane molecule by removing one hydrogen atom and include straight or branched moieties.

As used herein, "alkenyl" refers to a group of carbon and hydrogen atoms from an alkene molecule by removing one hydrogen atom and include straight or branched molecules. An alkenyl includes one or more carbon-carbon double bond.

As used herein, the term "saccharide group" refers to an oxidized, reduced or substituted saccharide monoradical covalently attached as group $R_3$ of the compound of formula (I) via any atom of the saccharide moiety, for example, via the aglycone carbon atom. The term includes amino-containing saccharide groups.

As used herein, the term "hexose" encompasses D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like.

As used herein, the term "pentose" encompasses D-ribose or D-arabinose; ketoses such as D-ribulose or D-fructose; disaccharides such as 2-O-(.alpha.-L-vancosaminyl)-.beta.-D-glucopyranose, 2-O-(3-desmethykalpha.-L-vancosaminyl)-.beta.-D-glucopyranose, sucrose, lactose, or maltose; derivatives such as acetals, amines, acylated, sulfated and phosphorylated sugars.

As used herein, the term "polysaccharide" encompasses (i) homo-polysaccharides consisting of a plurality of identical saccharide units and (ii) hetero-polysaccharides consisting of a plurality of saccharide units and at least two distinct saccharide units.

As used herein, the term "polysaccharide", which denotes a saccharide polymer comprising, or alternatively consisting of, 2 to 4 saccharide units, may be interchangeably used with the term "oligosaccharide".

The term "amino-containing saccharide group" refers to a saccharide group having an amino substitute. Representative amino-containing saccharides include L-vancosmine, 3-desmethyl-vancosamine, 3-epi-daunosamine, epi-vancosamine, acosamine, actinosamine, daunosamine, 3-epi-daunosamine, ristosamine, N-methyl-D-glucamine and the like.

In some preferred embodiments, in a glycerolipid of formula (I), $R_1$ is an alkyl or an alkenyl group having 16, 17 and 18 carbon atoms.

The results of the examples herein illustrate that the presence of the $R_1$ group having from 16 to 18 carbon atoms significantly contributes to the anti-metastatic effect of the glycerolipids of formula (I).

Without wishing to be bound by any particular theory, the inventors believe that the replacement of group $R_1$ by an alkyl or an alkenyl group having 15 carbon atoms or less will lead to glycerolipid compounds having a reduced ability to inhibit cell migration and thus a reduced anti-metastatic effect. In some embodiments of a compound of formula (I), $R_1$ is an alkyl group selected from the following alkyl groups: —$(CH_2)_{15}$—$CH_3$, —$(CH_2)_{16}$—$CH_3$ and —$(CH_2)_{17}$—$CH_3$.

In some embodiments of a compound of formula (I), $R_2$ is an hydroxy group.

In some other embodiments of a compound of formula (I), $R_2$ is of formula (II) and $R_{21}$, $R_{22}$ and $R_{23}$ are each an hydrogen atom.

In some other embodiments of a compound of formula (I), $R_2$ is of formula (II), and one among $R_{21}$, $R_{22}$ and $R_{23}$ is an alkyl group having one or two carbon atoms while the other two are each an hydrogen atom.

In some embodiments of a compound of formula (I), $R_3$ or $R_4$ is a monosaccharide selected from the group consisting of a pentosyl group and an hexosyl group.

Generally, according to the present invention, a pentose group has the following formula (V):

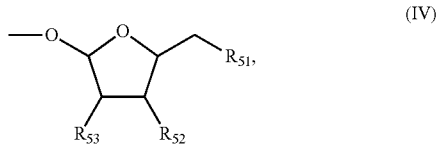

(IV)

wherein:
$R_{51}$, $R_{52}$ and $R_{53}$, one independently from each other, are selected from the group consisting of hydroxy, methoxy, acetyloxy, amino and acetylamino groups.

Preferred meanings for groups $R_{51}$, $R_{52}$ and $R_{53}$, are selected from hydroxy and acetyloxy.

In certain embodiments, $R_3$ or $R_4$ of formula (IV) have groups $R_{51}$, $R_{52}$ and $R_{53}$ which all denote an hydroxy group.

In other embodiments, $R_3$ or $R_4$ of formula (IV) have groups $R_{51}$, $R_{52}$ and $R_{53}$ which all denote an acetyl group.

In some preferred embodiments, $R_3$ or $R_4$ is a pentosyl selected from the group consisting of D-ribosyl, D-arabinosyl, D-xylosyl, D-ribulosyl and D-Xylulosyl.

Generally, according to the present invention, an hexosyl group has the following formula (V):

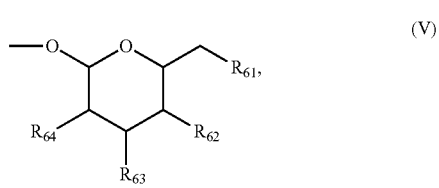

(V)

wherein:
$R_{61}$, $R_{62}$, $R_{63}$ and $R_{64}$, one independently from each other, are selected from the group consisting of hydroxy, methoxy, acetyloxy, amino and acetylamino groups.

Preferred meanings for groups $R_{61}$, $R_{62}$, $R_{63}$ and $R_{64}$, are selected from hydroxy and acetyloxy.

In certain embodiments, $R_3$ or $R_4$ of formula (V) have groups $R_{61}$, $R_{62}$, $R_{63}$ and $R_{64}$ which all denote an hydroxy group.

In other embodiments, $R_3$ or $R_4$ of formula (V) have groups $R_{61}$, $R_{62}$, $R_{63}$ and $R_{64}$ which all denote an acetyloxy group.

In some embodiments, $R_3$ or $R_4$ is an hexosyl selected from the group consisting of D-glucosyl, D-mannosyl and D-galactosyl.

In other embodiments, $R_3$ or $R_4$ is a ketohexosyl selected from the group consisting of a D-fructosyl and a D-sorbosyl.

In some embodiments, $R_3$ or $R_4$ is selected from the group consisting of β galactosyl and tetra-acetyl-β galactosyl groups.

In some other embodiments $R_3$ is selected from the group consisting of β glucosyl and tetra-acetyl-β glucosyl groups.

In still further embodiments, $R_3$ or $R_4$ is selected from the group consisting of inositol and N-acetylglucosamine.

As already specified previously in the present description, $R_3$ or $R_4$ may denote a polysaccharidyl group having from 2 to 4 saccharide units. In some embodiments, all saccharide units comprised in the said polysaccharidyl group are identical and the said polysaccararidyl group consists of a homopolysaccharidyl group. In other embodiments, the saccharide units comprised in the said polysaccharidyl group are not all identical and the said polysaccharidyl group consists of a heteropolysaccharidyl group.

Generally, in a $R_3$ or $R_4$ polysaccharidyl group of a compound of formula (I) according to the invention, any one of the saccharide units may be selected from the group of the saccharide units that are detailed above for the meanings of the monosaccharidyl units.

In some embodiments wherein $R_3$ or $R_4$ consists of a polysaccharidyl group comprising two or more hexose units, two hexose units are covalently bound through a 1-4 linkage or a 1-6 linkage. Two hexose units may be bound, one to the other, through a covalent bond selected from the group consisting of α1-4, α1-6, β1-4 and β1-6 linkages.

In some embodiments, $R_3$ or $R_4$ is a disaccharide selected from the group consisting of sucrosyl, lactosyl, maltosyl, melibiosyl, trehalosyl and cellobiosyl. Preferred embodiments encompass those wherein $R_3$ or $R_4$ is a disaccharide selected from the group consisting of lactosyl, maltosyl and melibiosyl.

In some other embodiments, $R_3$ or $R_4$ is a trisaccharide selected from the group consisting of raffinosyl and melezitosyl.

In still further embodiments, $R_3$ or $R_4$ is the tetrasaccharide acarbosyl.

Thus, according to certain embodiments of a compound of Formula (I), $R_3$ is selected from the group consisting of a monosaccharide group or a polysaccharide group having from 2 to 4 saccharide units.

Also, according to other embodiments of a compound of Formula (I), $R_3$ is a group of formula (III) previously defined herein, wherein $R_4$ is selected from the group consisting of a monosaccharide group or a polysaccharide group having from 2 to 4 saccharide units.

Preferred compounds of formula (I) according to the invention may be selected from the group consisting of the compounds (A) to (P) below:

Compound (A)

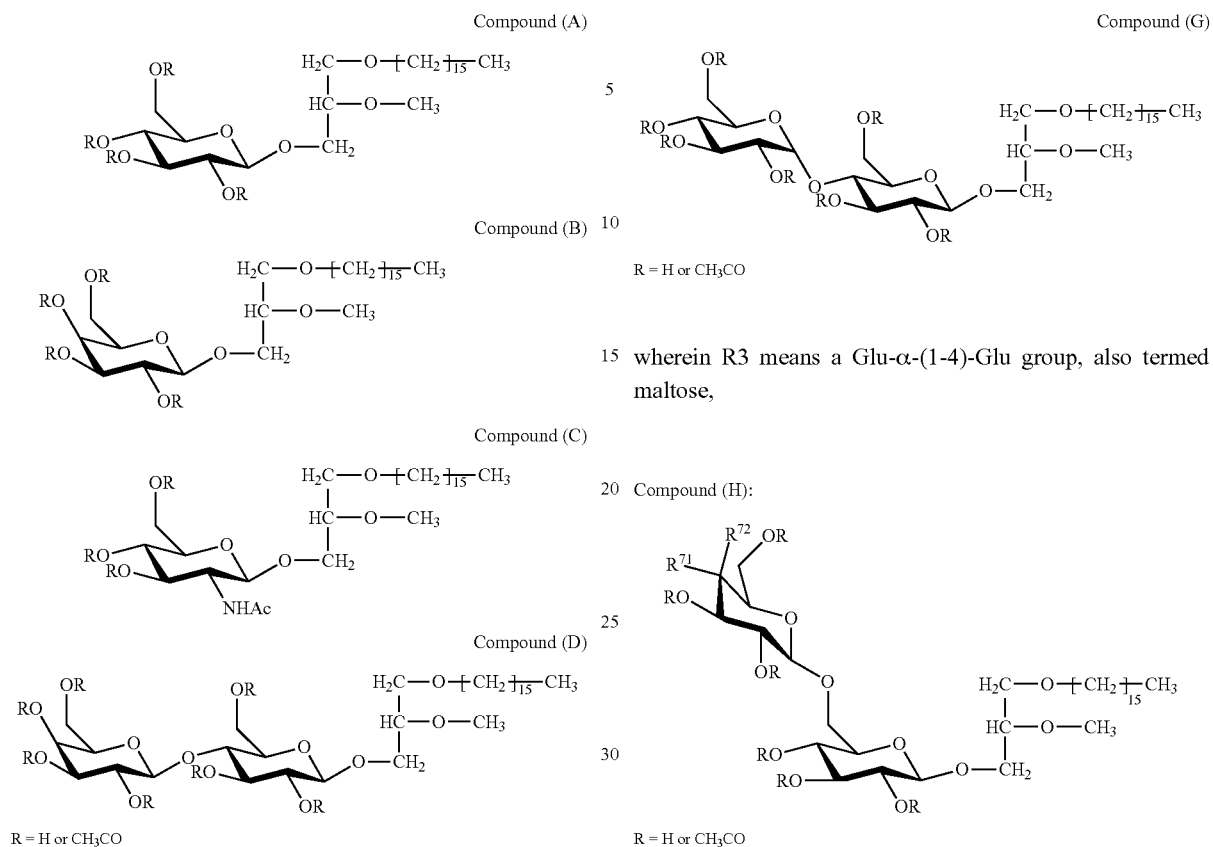

Compound (B)

Compound (C)

Compound (D)

R = H or CH₃CO wherein R3 means a Gal-β-(1-4)-Glu group, also termed lactose

Compound (E):

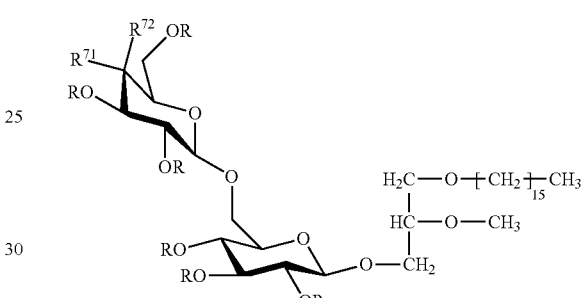

R = H or CH₃CO wherein R3 means a Gal-α-(1-4)-Glu group

Compound (F):

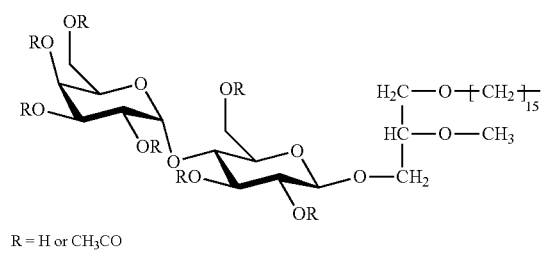

R = H or CH₃CO wherein R3 means a Glu-β-(1-4)-Glu group,

Compound (G)

R = H or CH₃CO wherein R3 means a Glu-α-(1-4)-Glu group, also termed maltose,

Compound (H):

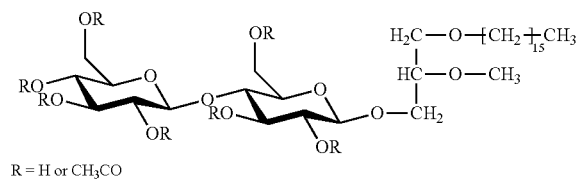

R = H or CH₃CO wherein $R^{71}$ and $R^{72}$ are independently selected from the group consisting of a hydrogen atom and a hydroxyl group or acetyl group, which encompasses (i) Gal-β-(1-6)-Glu when $R^{71}$ is H and $R^{72}$ is OH or OAcl and (ii) Glu-β-(1-6)-Glu when $R^{71}$ is OH or OAc and $R^{72}$ is H, Compound (I):

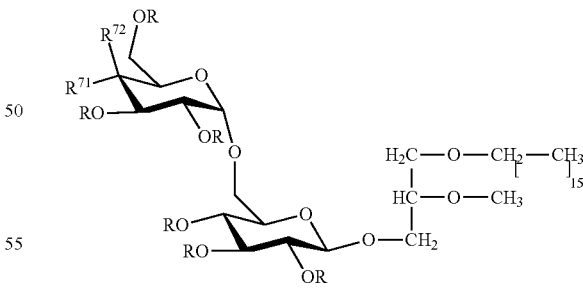

R = H or CH₃CO wherein $R^{71}$ and $R^{72}$ are independently selected from the group consisting of a hydrogen atom and a hydroxyl group or acetyl group, which encompasses (i) Gal-α-(1-6)-Glu when $R^{71}$ is H and $R^{72}$ is OH or OAc, also termed melibiose or acetylmelibiose and (ii) Glu-α-(1-6)-Glu when $R^{71}$ is OH or OAc and $R^{72}$ is H, Compound (J):

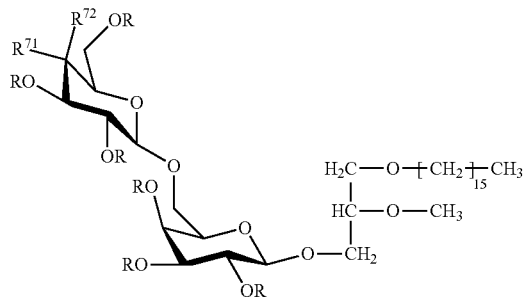

R = H or CH₃CO wherein $R^{71}$ and $R^{72}$ are independently selected from the group consisting of a hydrogen atom and a hydroxyl group or acetyl group, which encompasses (i) Gal-β-(1-6)-Gal when $R^{71}$ is H and $R^{72}$ is OH or OAc and (ii) Glu-β-(1-6)-Gal when $R^{71}$ is OH or OAc and $R^{72}$ is H Compound (K):

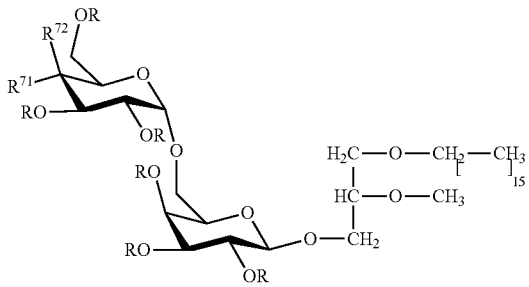

R = H or CH₃CO wherein $R_{71}$ and $R_{72}$ are independently selected from the group consisting of a hydrogen atom and a hydroxyl group or acetyl group, which encompasses (i) Gal-α-(1-6)-Gal when $R_{71}$ is H and $R_{72}$ is OH or OAc and (ii) Glu-α-(1-6)-Gal when $R_{71}$ is OH or OAc and $R_{72}$ is H, Compound (L):

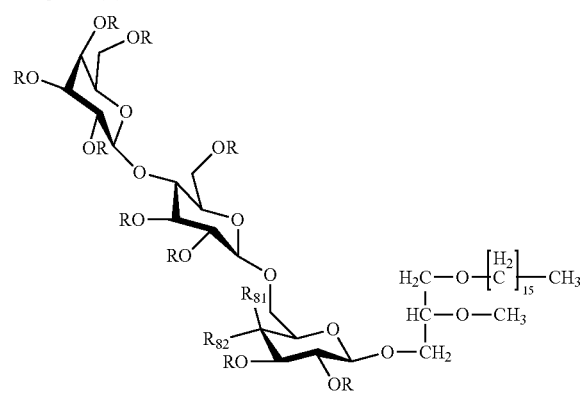

R = H or CH₃CO

Compound (M):

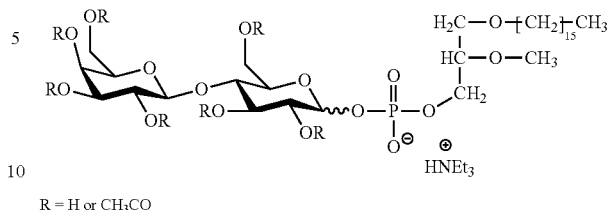

R = H or CH₃CO wherein $R_4$ means a Gal-β-(1-4)-Glu group, also termed lactose or acetyllactose, Compound (N):

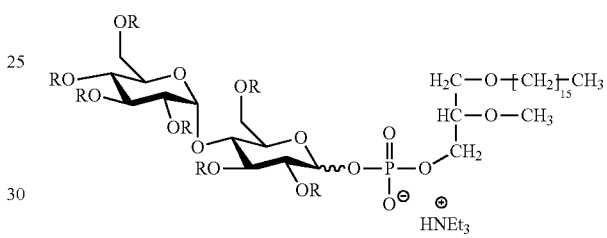

R = H or CH₃CO wherein $R_4$ means a Glu-α-(1-4)-Glu group, also termed maltose or acetylmaltose, Compound (O):

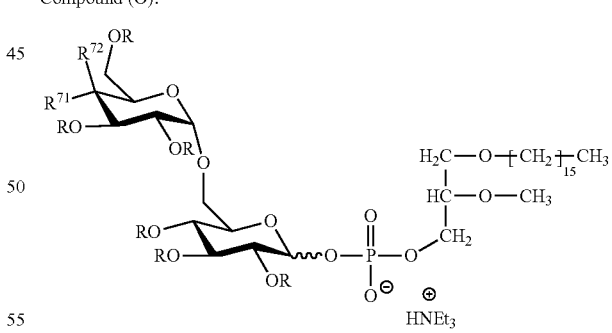

R = H or CH₃CO wherein $R^{71}$ and $R^{72}$ are independently selected from the group consisting of a hydrogen atom and a hydroxyl group or acetyl, which encompasses (i) Gal-α-(1-6)-Glu when $R^{71}$ is H and $R^{72}$ is OH or OAc, also termed melibiose or acetylmelibiose, and (ii) Glu-α-(1-6)-Glu when $R^{71}$ is OH or OAc and $R^{72}$ is H, Compound (P):

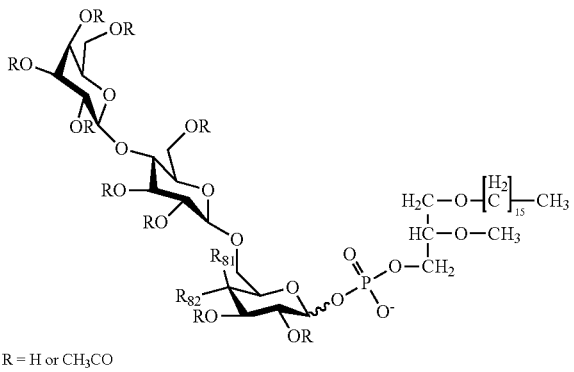

R = H or CH₃CO wherein $R^{81}$ and $R^{82}$ are independently selected from the group consisting of a hydrogen atom and a hydroxyl group or acetyl group, which encompasses (i) lactose-β- or acetyllactose-β-(1-6)-Glu when $R^{81}$ is H and $R^{82}$ is OH or OAc and (ii) lactose-β- or acetyllactose-β-(1-6)-Gal when $R^{81}$ is OH or OAc and $R^{82}$ is H.

Illustratively:

Compound A is illustrated notably by compounds JPH1518 and JPH 1523 disclosed in Table 1 and Table 2, Compound B is illustrated notably by compounds JPH1519 and JPH 1524 disclosed in Table 2, Compound C is illustrated notably by compound JPH1528 disclosed in Table 1 and Table 2, Compound D is illustrated notably by compound JPH1701 disclosed in Tables 1, 2 and 3 and compound JPH1700 disclosed in Table 3, Compound G is illustrated notably by compound JPH1800 disclosed in Table 3, Compound I is illustrated notably by compounds JPH1784 and JPH1882 disclosed in Table 3, and Compound M is illustrated notably by compound CHS31 disclosed in Table 3, For performing the synthesis of a compound of formula (I), the one skilled in the art may refer to the following references:

J. J. Godfroid, C. Broquet, S. Jouquey, M. Lobbar, F. Heymanns, C. Redeuith, E. Steiner, E. Michel, E. Coeffier, J. Fichelle and M. Worcel. *J. Med. Chem.* 1987, 30, 792-797, R. R. Schmidt *Angew. Chem.* 1986, 98, 213-236, R. R. Schmidt *Pure and Appl. Chem.* 1989, 61, 1257-1270, N. S. Chandrakumar and J. Hajdu *J. Org. Chem.* 1983, 48, 1197-1202, R. K. Erukulla, X. Zhou, P. Samadder, G. Arthur, and R. Bittman *J. Med. Chem.* 1996, 39, 1545-1548, and J. R. Marino-Albernas, R. Bittman, A. Peters, and E. Mayhew *J. Med. Chem.* 1996, 39, 3241-3247

M. Hunsen, D. A. Long, C. R. D'Ardenne, and A. L. Smith *Carbohydr. Res.* 2005, 340, 2670-2674

S. Chittaboina, B. Hodges, and Q. Wang *Lett. Org. Chem.* 2006, 3, 35-38

P. J. Garegg, T. Regberg, J. Stawinsky, and R. Strömberg. *Chem. Scr.* 1986, 25, 59-62

B. C. Froehler and M. D. Mattenci *Tetrahedron Lett.* 1986, 27, 469-472

A. V. Nikolaev, I. A. Ivanova, V. N. Shibaev, and N. K. Kochetkov. *Carbohydrate Research* 1990, 204, 65-78

I. A. Ivanova, A. J. Ross, M. A. J. Ferguson, and A. V. Nikolaev *J. Chem. Soc., Perkin Trans* 1 1999, 1743-1753

A. J. Ross, I. A. Ivanova, M. A. J. Ferguson and A. V. Nlkolaev *J. Chem. Soc., Perkin Trans.* 1, 2001, 72-81.

Illustratively, methods for the synthesis of substituted glyceroplipids are disclosed notably in the U.S. Pat. No. 6,030,628, to which the one skilled in the art may refer for performing the synthesis of a compound of formula (I) according to the invention.

Other methods for the synthesis of substituted glycerolipids are also disclosed in the US patent applications or patents no US 2004/0067893, US 2004/0213836, U.S. Pat. No. 4,275,588, U.S. Pat. No. 5,932,242, U.S. Pat. No. 5,762,958, U.S. Pat. No. 6,583,127.

The embodiments of a compound of formula (I) wherein group $R_3$ denotes a monosaccharide group or a polysaccharide group may also be synthesized as it is described hereunder. The method hereunder may be used for synthesizing any one of the saccharide derivatives encompassed in the family of compounds having formula (I):

a) Synthesis of the Glycerol-Diether Derivative

Compound A is the glycerol-lipid precursor used for the attachment of the saccharide unit (See M. Kates et al. *Lipids*, 1991, 26, 1095-1101; J. J. Godfroid et al. *J. Med. Chem.* 1987, 30, 792-797.). Its synthesis is depicted on scheme 1 presented in FIG. 1.

Scheme 1 of FIG. 1: (i) $C_{16}H_{33}Br$, NaH, Toluene reflux 6 h; (ii) HCl 12M, MeOH reflux 3 h; Ph₃Cl, Et₃N, Toluene reflux 5 h; (iv) (a) CH₃I, NaH, THF reflux 3 h; (b) HCl 12M, MeOH/CHCl₃ rt.

b) Synthetic Pathway of Di-Saccharide with an α Anomeric Linkage.

Figure 2:
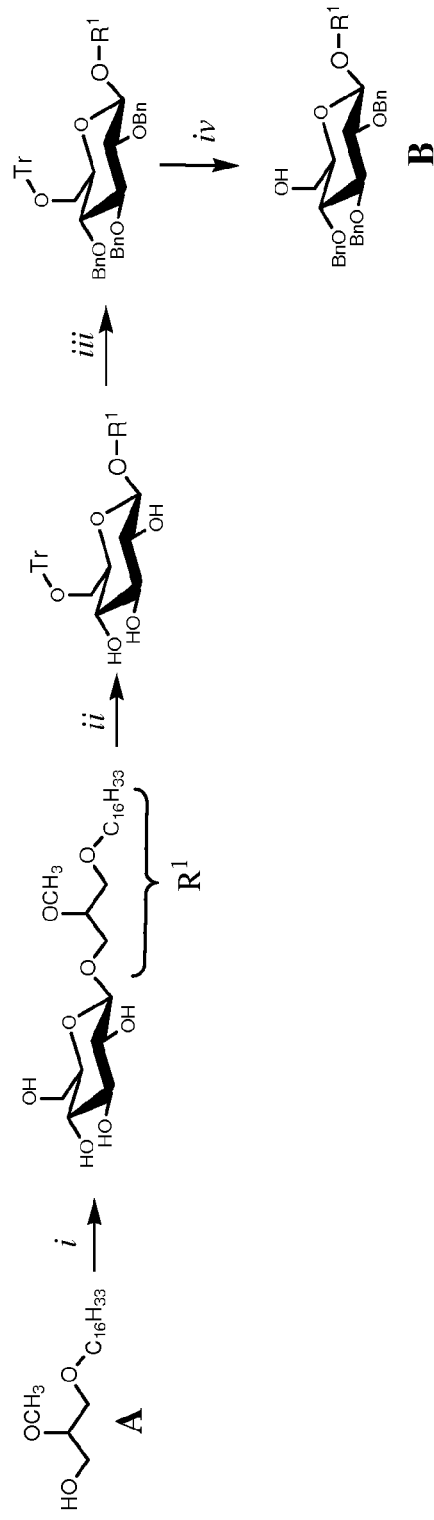
FIG. 2 illustrates a scheme of synthesis of the intermediate compound B that is a glycopyranosyl derivative with a free hydroxyl group in position 6, useful for obtaining a compound of formula (I) wherein group $R_3$ denotes a monosaccharide or a polysaccharide group. This scheme is termed "scheme 2" in the present specification.

First, the synthesis of the glycopyranosyl derivative, with a free hydroxyl group in position 6 (compound B), will be synthesised as schematised in FIG. 2.

Scheme 2 of FIG. 2: (i) Glycosyl-tetraacetate-trichloroacetamidate, BF₃, Et₂O (ii) Ph₃Cl, Et₃N, Toluene reflux 5 h; (iii) BnBr, NaH, DMF 12H; (vi) HCl 12M, MeOH/CHCl₃ rt (See R. R. Schmidt *Angew. Chem.* 1986, 98, 213-236; R. R. Schmidt *Pure and Appl. Chem.* 1989, 61, 1257-1270).

Figure 3:
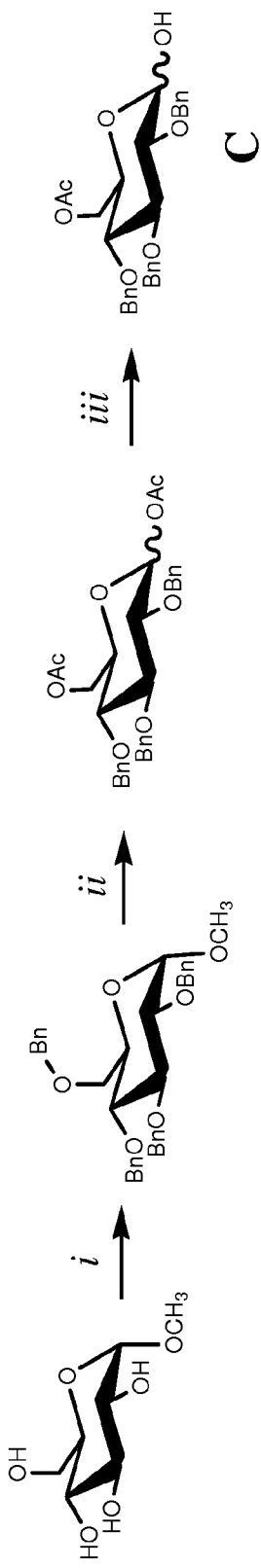
FIG. 3 illustrates a scheme of synthesis of the intermediate compound C that is a 6-O-acetyl-2'3'4-tri-O-benzyl-D-galactopyranose, useful for obtaining a compound of formula (I) wherein group $R_3$ denotes a monosaccharide or a polysaccharide group. This scheme is termed "scheme 3" in the present specification.

Then, the second saccharide unit (C) the 6-O-acetyl-2'3'4-tri-O-benzyl-D-galactopyranose possessing the correct protecting groups will be synthesised as reported in FIG. 3.

Scheme 3 of FIG. 3: (i) BnBr, NaH, DMF 12H; H₂SO₄, Ac₂O/AcOH 3 h rt; (iii) BnNH₂, THF rt 15 h.

The α glycosylation will be achieved by reaction of B with C (see scheme 4 and Shingu et al. *Carbohyd. Res.* 2005, 340, 2236-2244). After a deprotecting step, the expected compound will be produced, as illustrated in FIG. 4.

Figure 4:
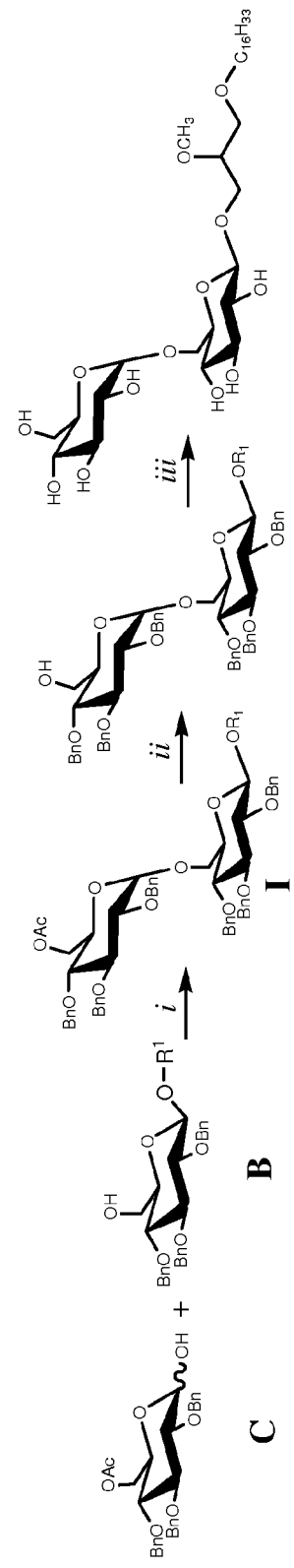
FIG. 4 illustrates a scheme of synthesis of a compound of formula (I) wherein group $R_3$ denotes a monosaccharide or a polysaccharide group, by reacting compound C with compound B. This scheme is termed "scheme 4" in the present specification.

Scheme 4 of FIG. 4: (i) Ph₃P, CBr₄, DMF; (ii) MeONa cat., MeOH; (iii) H₂, Pd/C, MeOH The selective deprotection of the acetate group in position 6 of the intermediate I represented in FIG. 4, will readily offer the possibility to introduce either a third saccharide unit, and similarly subsequently of a fourth saccharide unit.

Figure 5:
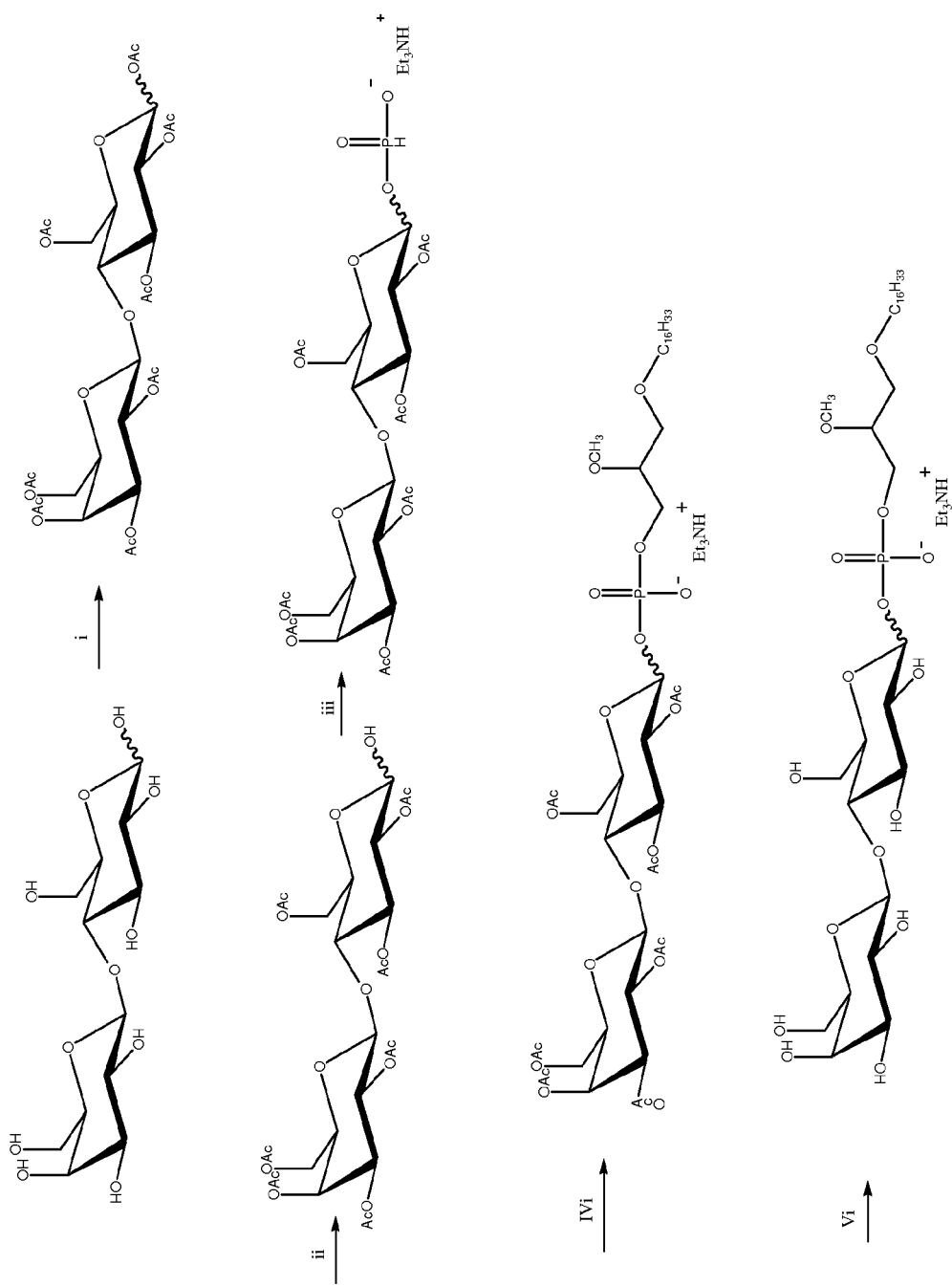
FIG. 5 illustrates a scheme of synthesis of a compound of formula (I) wherein group $R_3$ is of formula (III) and wherein $R_4$ denotes a monosaccharide or a polysaccharide group. This scheme is termed "scheme 5" in the present specification.

Scheme 5 of FIG. 5: (i) acetic anhydride/HClO₄, Acetic acid, 15H, ((ii) Ammonium acetate, DMF, 48H, (iii) Imidazole/PCl₃/Et₃N, CH₃CN, (IVi) A, Pivaloyl Chloride, I₂, Pyridine, (Vi) (a) NaOCH₃ cat., CH₃OH, (b) Amberlite IR 120.

As it has been already specified above, beyond their low cytotoxicity, the compounds of formula (I) according to the invention primarily induce an inhibition or even a blocking of the SK3/KCa2.3 channel activity.

Also, the compounds of formula (I) according to the invention primarily exhibit a high inhibiting activity of cancerous cell migration and thus have been found useful for inhibiting cancer metastasis. Further, the in vivo anti-metastatic properties of a glycerolipid of formula (I) have also been shown.

A compound of formula (I) as described herein is useful for preventing the occurrence of metastasis in cancers where cancer cells express SK3/KCa2.3 channel.

Particularly, a compound of formula (I) as described herein is useful for preventing the occurrence of metastasis in various cancers which include, but are not limited to, apudoma, choristoma, branchioma, malignant carcinoid syndrome, carcinoid heart disease, carcinoma (e.g., Walker, basal cell, basosquamous, Brown-Pearce, ductal, Ehrlich tumour, in situ, Krebs 2, Merkel cell, mucinous, non-small cell lung, coat cell, papillary, scirrhous, bronchiolar, bronchogenic, squamous cell, and transitional cell), histiocytic disorders, leukaemia (e.g. B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumours, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chondroma, cranio-pharyngioma, dysgerminoma, hamartoma, mesenchymoma, mesonephroma, myosarcoma, ameloblastoma, cementoma, odontoma, teratoma, thymoma, trophoblastic tumour, adenocarcinoma, carcinoma, adenoma, cholangioma, cholesteatoma, cylindroma, cystadenocarcinoma, cystadenoma, granulosa cell tumour, gynandroblastoma, hepatoma, hidradenoma, islet cell tumour, Leydig cell tumour, papilloma, Sertoli cell tumour, theca cell tumour, leiomyoma, leiomyosarcoma, myoblastoma, myoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma phyl lodes, fibrosarcoma, hemangiosarcoma, leiomyosarcoma, leukosarcoma, liposarcoma, lymphangiosarcoma, myosarcoma, myxosarcoma, osteosarcoma, ovarian carcinoma, rhabdomyosarcoma, sarcoma (e.g. Ewing, experimental, Kaposi, and mast cell), neoplasms (e.g. bone, breast, digestive system, liver, pancreatic, pituitary, testicular, orbital, head and neck, central nervous system, acoustic, pelvic, respiratory tract, and urogenital), neurofibromatosis, and cervical dysplasia, and for treatment of other conditions in which cells have become immortalized or transformed. These latter results also support the effectiveness of a glycerolipid of formula (I), irrespective of the kind of cancer in which the occurrence of metastasis is to be prevented or treated.

The invention could be used in combination with other treatment modalities, such as chemotherapy, cryotherapy, hyperthernia, radiation therapy, and the like.

A glycerolipid of formula (I) may be used for preventing the occurrence of metastasis in any body tissue or in any body organ. The usefulness of a glycerolipid of formula (I) encompasses preventive or therapeutic treatments against the occurrence of metastasis in a wide variety of tissues and organs including ovary, uterus, kidney, liver, lung, bone tissue (e.g. leg bones including femur, arm bones, spinal column including dorso-lumbar vertebra, pelvis), spleen, lymph nodes, colon, breast, brain, prostate, pancreas and skin.

In some embodiments, the compounds of formula (I) as described herein are useful for preventing the occurrence of metastasis in cancer patients affected with a melanoma or a breast cancer, a lung cancer, a thyroid cancer, an osteosarcoma or a kidney cancer.

Another object of the present invention consists of a compound of formula (I) per se as described throughout the instant specification.

A further object of the present invention consists of a pharmaceutical composition comprising a compound of formula (I) as defined throughout the instant specification in combination with one or more pharmaceutically excipients.

A still further object of the present invention consists of a pharmaceutical composition for preventing cancer metastasis comprising a compound of formula (I) as defined throughout the instant specification in combination with one or more pharmaceutically excipients.

A yet further object of the present invention consists of the use of a compound of formula (I) as described herein for the manufacture of a medicament for preventing the occurrence of metastasis in a cancer patient;

Another object of the present invention consists of the use of a compound of formula (I) as described herein for preventing the occurrence of metastasis in a cancer patient.

Pharmaceutical compositions comprising a compound of formula (I) as well as methods for therapeutic administration of a compound of formula (I) are described hereafter.

Pharmaceutical Compositions According to the Invention

The present invention provides for pharmaceutical compositions comprising an effective amount of a compound of formula (I) as described in the present specification, and a pharmaceutically acceptable carrier.

Suitable carriers and their formulations are described in Remington's Pharmaceutical Science, 16$^{th}$ ed.; 1980, Mack publishing Co, edited by Oslo et al.

By <<physiologically acceptable carrier>> is meant solid or liquid filler, diluents or substance, which may be safely used in systemic or topical administration. Depending on the particular route of administration, a variety of pharmaceutically acceptable carriers well known in the art include solid or liquid fillers, diluents, hydrotopes, surface active agents, and encapsulating substances.

These compositions will typically contain an effective amount of a compound of formula (I), together with a suitable amount of carrier to prepare pharmaceutically acceptable compositions suitable for effective administration to the patient.

The pharmaceutical composition according to the invention may be administered parenterally or by other methods that ensure its delivery to the bloodstream in an effective form. Dosages and desired drug concentrations of such pharmaceutical compositions may vary depending on the particular use envisioned.

Sterility is readily accomplished by sterile filtration through (0.2 micron) membranes.

The pharmaceutical composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The amount of the compound of formula (I) to be administered will be governed by such considerations, and is the minimum amount necessary to reduce or block the occurrence of cancer metastasis in a patient or a mammal.

The amount of the compound of formula (I) to be parenterally administered at each dose will typically vary from 0.01 mg/kg to 100 mg/kg, preferably from 0.01 mg/kg to 50 mg/kg, and most preferably 0.05 mg/kg to 25 mg/kg, and for example 10 mg/kg.

Generally, a pharmaceutical composition according to the invention comprises from 0.01% to 99.99% by weight, alternatively from 0.1% to 99.9% by weight, further alternatively from 1% to 99% by weight, yet alternatively from 10% to 90%, of a compound of formula (I), based on the total weight of the said pharmaceutical composition, the remaining of the composition consisting of one or more excipients comprised therein.

Such amount is preferably below the amount that is toxic to the mammal.

Methods of Treatment According to the Invention

The present invention provides for methods for the prevention of cancer metastasis.

This invention provides for methods for the prevention of the occurrence of cancer metastasis in a patient, comprising contacting a cell with an effective amount of a compound of formula (I), such as disclosed above.

An "effective amount" thus encompasses amounts of a compound of formula (I) that decreases the number of metastases in vivo. A decrease in the number of metastases in vivo may be assessed according to the experimental model assays disclosed in the examples herein.

Illustratively, an effective amount of a compound of formula (I) may be assessed by a method comprising the steps of:
a) providing a plurality of animals,
b) administering to the animals provided at step a) a desired number of non-metastatic cancer cells wherein the said cancer cells have the ability to generate metastasis,
c) administering a known amount of a compound of formula (I) to the animals obtained at the end of step b),
d) measuring the number of metastatic cancer cells in one tissue type or more than one tissue type of the animals obtained at the end of step c),
e) comparing, for each type of tissue tested, the number of metastatic cancer cells with the number of metastatic cancer cells that is found in control animals which have been subjected to step b) but which have not been administered with the said compound of formula (I), and
f) assigning the said known amount of a compound of formula (I) as an effective amount of the said compound if the number of metastatic cancer cells that is found in at least one tissue type from the animals which have received the said known amount of a compound of formula
(I) is lower than the number of metastatic cancer cells that is found in control animals which have not been administered with the said compound of formula (I), According to some preferred embodiments of the method above, the animals used at step a) consist of mice, including nude mice, e.g. nude mice form the NMRI strain.

According to some preferred embodiments of the method above, the non-metastatic cancer cells that are administered at step b) consist of cancer cells originating from an animal of the same species than the animal provided at step a), e.g. mice cancer cells.

Preferably, the said non-metastatic cancer cells are administered intravenously, so that these cells are enabled to colonize rapidly in one or more tissue or organ of the animal body.

According to some preferred embodiments, the said non-metastatic cancer cells that are administered at step b) consist of non-metastatic breast cancer cells. Illustratively, the intravenous injection of non-metastatic breast cancer cells will lead to the homing of the said non-metastatic cancer cells in the breast tissue where the said cancer cells then proliferate, which equates to a grafting of a non-metastatic cancer tumor within the breast tissue of the animals.

According to some preferred embodiments of the method above, it is provided at step a) a number of test animals that allows the simultaneous testing of a serial of known amounts of the compound of formula (I). In other words, the animals provided at step a) may be divided into sub-groups of animals, wherein each sub-group of animals receives at step c) a given known amount of the compound of formula (I), thus allowing to assay simultaneously a range of amounts of the compound of formula (I), so as to determine the minimal effective amount of the said compound of formula (I) that inhibits metastasis at the end of the in vivo assay. Preferably, one of the sub-groups of animals consists of a control group that is administered with the non-metastatic cancer cells at step b) but is not administered with the compound of formula (I) at step c). The number of non-metastatic cancer cells measured in the said control sub-group of animals is then used for performing the comparison step e).

At step f) of the method above, test animals are considered to bear a lower number of metastatic cells than the animals from a control sub-group if the difference in the number of metastatic cells is statistically significant, which means that, in a conventional T-test, the P value is lower that 0.05, which encompasses a P value lower than 0.01.

As used herein, the "number of metastatic cancer cells" that is measured at step d) encompasses the number of metastasis focuses that are found in the animals. In some embodiments, the "number of metastatic cells" encompasses the number of metastasis focuses for each type of tissue tested, or body localization tested, that are found in the animals. Thus, in some embodiments, the "number of metastatic cancer cells" that is measured at step d) encompasses for each type of tissue, e.g. ovary, uterus, kidney, liver, lung, leg, spinal column, spleen and lymph node, the number of metastatic cell focuses.

As used herein, the "number of metastatic cancer cells" that is measured at step d) may be performed by quantifying a detectable signal emitted by the said metastatic cancer cells and then comparing the corresponding signal quantification signal values at step e). The said detectable signal encompasses a bioluminescence signal that is emitted by the said metastatic cancer cells. Illustratively, as it is shown in the examples herein, the said bioluminescence signal may be obtained by administering to the mice a potassium salt of a bioluminescent substance, e.g. a potassium salt of D-luciferin, and then localizing and quantifying the bioluminescence signal emitted by the whole animal body, e.g. by using a whole-body bioluminescence imager apparatus.

Finally, once determined an effective amount of a compound of formula (I) by the method above, which effective amount may be expressed as the effective amount by weight unit of the animal body, e.g. the amount per kg of body weight, the one skilled in the art readily determines the effective amount of the said compound of formula (I) for preventing the occurrence of metastasis in a human cancer patient, including in most instances the treatment regimen.

As already described previously herein, the amount of a compound of formula (I) to be administered at each dose will typically vary from 0.01 mg/kg to 100 mg/kg, preferably from 0.01 mg/kg to 50 mg/kg, and most preferably 0.05 mg/kg to 25 mg/kg, and for example 10 mg/kg.

The administration regimen cycle encompasses daily, bi-weekly, weekly, bi-monthly and monthly administration of a compound of formula (I).

The present invention also provides methods for preventing metastasis from a primary cancer, comprising administering to the subject, a compound of formula (I). In a preferred aspect, the compound is substantially purified. The subject is preferably an animal, and is preferably a mammal, and most preferably human.

Various delivery systems are known and can be used to administer a compound of formula (I), e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432). Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Pulmonary administration can also be employed, e.g., by use of an inhaler or nebulizer, and formulation with an aerosolizing agent.

In a specific embodiment, it may be desirable to administer the compositions of the invention locally to a specific area of the body; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In some other embodiments, a compound of formula (I) may be specifically targeted to one or more tissues, e.g. encapsulated in liposomes coated with polyethylene glycol or having at their surface ligand molecules that bind with surface molecules (e.g., surface antigens, surface glycoside residues, surface receptors, etc.) expressed by metastatic cancer cells.

The present invention is further illustrated by, without being limited to, the examples below.

EXAMPLES

Example 1

In Vitro Anti-Metastatic Activity of Glyceroplids

A. Materials and Methods
A.1. Cell Culture

The human mammary cancer cell line MDA-MB-435s was grown in Dulbecco's modified Eagle's medium (DMEM) containing 5% fetal bovine serum (FBS) as already described (Roger S, Potier M, Vandier C, Le Guennec J Y, Besson P. Description and role in proliferation of iberiotoxin-sensitive currents in different human mammary epithelial normal and cancerous cells. Biochim Biophys Acta 2004; 1667: 190-9.). The immortalized normal mammary epithelial cell lines MCF-10A and 184A1 were cultured in DMEM/Ham's F-12, 1:1 mix containing 5% horse serum (Invitrogen Life Technologies, France), insulin (10 µg/ml), epidermal growth factor (20 ng/ml), hydrocortisone (0.5 µg/ml) and, respectively for MCF-10A and 184A1, 100 ng/ml cholera toxin and 1 ng/ml cholera toxin plus 5 µg/ml transferrin.

High $K^+$ medium was custom made from $K^+$-, $Na^+$- and $Ca^{2+}$-free DMEM-based medium (Cambrex Bio Science, France) and supplemented at time of use at 60 mM KCl, 84 mM NaCl, 2 mM $CaCl_2$.

All cell lines were obtained from the American Type Culture Collection (ATCC, LGC Promochem, Molsheim, France).

A.2. Cell Proliferation and Cell Migration In Vitro.

Cell proliferation was determined using the tetrazolium salt reduction method, as described (Roger S, Potier M, Vandier C, Le Guennec J Y, Besson P. Description and role in proliferation of iberiotoxin-sensitive currents in different human mammary epithelial normal and cancerous cells. Biochim Biophys Acta 2004; 1667:190-9.). Cells were seeded on 24-well plates and grown for 48 h. Drugs were then added for 24 h at concentrations that had no effect on cell proliferation. Cell migration was analyzed in 24-well plates receiving 8-µm pore size polyethylene terephtalate membrane cell culture inserts (Becton Dickinson, France), as described (Roger S, Potier M, Vandier C, Le Guennec J Y, Besson P. Description and role in proliferation of iberiotoxin-sensitive currents in different human mammary epithelial normal and cancerous cells. Biochim Biophys Acta 2004; 1667:190-9.).

Wound healing assay: Cells were seeded in culture dishes and grown until confluence in DMEM supplemented with 10% foetal calf serum. The monolayer was scratched with a sterile yellow pipette tip. The migration of cells to the cleared area was inspected under a microscope. Pictures were taken directly at the time of scratching and after 24 h.

A.3. Cytotoxic Assays.

To distinguish between a cytostatic and a cytotoxic effect, two cytotoxic assays were used. In the first one cell viability after 24 h of treatment was assessed by the Trypan blue exclusion method. In the second method cells were incubated with edelfosine at 1, 3, 10 and 30 µM for 8 h, and then washed three times with fresh culture medium. The remaining viable cells were allowed to grow for 6 days before being quantified using the MTT assay as described above.

A.4. Solutions and Drugs.

The physiological saline solution (PSS) had the following composition (in mM): NaCl 140, $MgCl_2$ 1, KCl 4, $CaCl_2$ 2, D-glucose 11.1, and HEPES10, adjusted to pH 7.4 with NaOH 1 M. The pipette solution, pCa=7 (free $Ca^{2+}$ concentration), had the following concentration (in mM): K-glutamate 125, KCl 20, $CaCl_2$ 0.37, $MgCl_2$ 1, Mg-ATP 1 EGTA 1, HEPES10, adjusted to pH 7.2 with 1M KOH. Pipette solutions with higher pCa (6.4 and 6) are also used. Tetraethylammonium (TEA), 4-aminopyridine (4-AP), NS 1619 (1-(2'-hydroxy-5'-trifluoro methylphenyl)-5-trifluoromethyl-2(3H)benzimidazolone)), Apamin, BMS 204-352 and edelfosine were added to the PSS or culture media at the concentrations indicated in the figure legends. Except for BMS 204-352 which was kindly given by Dominique Cahard (UMR 6014 CNRS de l'IRCOF University of Rouen), all drugs and chemicals were purchased from Sigma-Aldrich (St Quentin, France).

A.5. Statistics.

Unless otherwise indicated, data were expressed as mean±standard error of the mean (n=number of cells). Statistical analysis, performed with StatView 4.57 software (Abacus Concepts, Berkeley, USA) was made using Student t-test or one-way factor ANOVA followed by post hoc Bonferroni-Dunn test. Differences were considered significant when $p<0.05$.

B. Results

The results showing (i) the low cytotoxicity and (ii) the high cell migration inhibitory activity of various glycerolipid compounds of formula (I) towards metastasizing cancerous cells are depicted in Table I hereafter.

Example 2

In Vitro and In Vivo Anti-Metastatic Activity of Glyceroplids

A. Materials and Methods

A.1. Cell Culture

For this study two cell lines were used MDA-MB-435s and HEK293 which were purchased from ATCC. These cell lines were maintained in Dulbecco's Modified Eagle's Medium. Culture media were supplemented with 5% (v/v) and 10% of foetal bovine serum (FBS) for MDA-MB-435s and HEK293 respectively. Cells were grown in a humidified atmosphere at 37° C. (95% air, 5% $CO_2$). The absence of mycoplasma contamination was to verified regularly using the Mycoalert® Mycoplasma Detection Kit (Lonza).

A.2. Constructs, Transfection and Transduction

All constructs as previously described (Chantome et al., Exp Cell Res. 2009 Dec. 10; 315(20):3620-30).

MDA-MB-435s and HEK293 cells were transduced with lentiviral vector at multiplicities of infection (MOI) of 1 to 3 in the presence of polybrene (4 µg/ml, Sigma). The transduction rate for MDA-MB-435s determined by counting GFP cells was close to 90%. In order to selection one clone of HEK293-SK3/KCa2.3 limit dilution were realized and each clone was tested in patch clamp with apamin and edelfosine and by western blotting in order to control expression of SK3/KCa2.3 channel.

A.3. Cell Proliferation Assays

Cell proliferation was determined using the tetrazolium salt reduction method (MTT), as described elsewhere (S. Roger et al., 2004). Cells were seeded on 24-well plates at a density of 40,000 cells per well and measurements were performed in triplicate 24 hours after implantation.

A.4. Two-Dimensional (20) Motility Assays

Cell motility was analyzed in 24-well plates receiving 8-µm pore-size polyethylene terephthalate membrane cell culture inserts (Becton Dickinson, France), as previously described ((S. Roger et al., 2004). Briefly, $4 \times 10^4$ MDA-MB-435s cells were seeded in the upper compartment with medium culture supplemented with 5% of FBS (±molecules). The lower compartment was filled with medium culture supplemented with 10% FBS (±molecules) as a chemoattractant. Two-dimensional motility assays were performed without coating. After 24 h. stationary cells were removed from the topside of the membrane, whereas migrated cells in the bottom side of the inserts were fixed, stained, and counted in five different fields (magnification, ×200). At least three independent experiments were each performed in triplicate.

A.5. Electrophysiology

Experiments were performed with cells seeded into 35-mm Petri dishes at 3000 cells per cm2. All experiments were performed using the conventional whole-cell recording configuration of the patch-clamp technique as previously described [8]. PCa solution was 7 and 6.4 respectively for MDA-MB-435s and HEK293-SK3/KCa2.3 cells.

Briefly, experiments were conducted using Axopatch 200B patch-clamp amplifier (Axon Instrument) and data, digitized with 1322-A Digidata converter (Axon Instrument), were stored on a computer using Clampex of pClamp 9.2 software (Axon Instru-ment). The patch-clamp data was analyzed using both Clampfit 9.2 and Origin 7.0 software (Microcal Inc., Northampton, Mass., USA).

A.6. Solutions and Drugs

The physiological saline solution (PSS) had the following composition (in mM): NaCl-140, $MgCl_2$ 1, KCl 4, $CaCl_2$ 2, D-glucose 11.1 and HEPES 10, adjusted to pH 7.4 with NaOH.

The pipette solution for the whole-cell recordings contained (in mM): K-glutamate 125, KCl 20, $MgCl_2$ 1, Mg-ATP 1, HEPES 10, and pH was adjusted to 7.2 with KOH and various concentrations of $CaCl_2$ and EGTA were added to obtain calculated pCa=7 (0.37 mM $CaCl_2$ and 10 mM EGTA) or pCa=6.4 (0.7 mM $CaCl_2$ and 1 mM EGTA).

The alkyl-lipids molecules were dissolved in a mix ethanol/DMSO. Final concentrations were lower than 2 and 3% respectively for ethanol and DMSO.

A.7. Experimental Metastasis Assays and Treatment with JPH1701

Female NMRI nude mice, 6 weeks old, were purchased from Janvier laboratories. Mice were bred and housed at INSERM, U892, University of Nantes, under the animal care license no 44565.

MDA-MB-435s were incubated with 1 µM JPH1701 or with 2% DMSO/3% ethanol (vehicle) during 24 h and injected (0.75 106) in iv into the lateral tail vein. Next, mice were treated three times a week for 12 weeks with JPH1701 at 15 mg/kg in i.v. or with vehicle. No adverse effects were observed in mice treated with JPH1701 or vehicle.

A.8. Mammary Fat-Pad-Model Tumor:

Female NMRI nude mice, 3-4 weeks old, were purchased from Janvier laboratories. Mice were bred and housed at Inserm, U892, University of Nantes, under the animal care license no 44565.

The luciferase expressing cell line MDA-MB-435s- were treated with 1 µM JPH 1701 (Ohmline) or with 2% DMSO/3% ethanol (vehicle) for 24 h and 2.106 cells were injected into the right cleared fat pad. The cells were injected in a volume of 50 µL of DMEM without serum through a 25-gauge needle. Mice were treated three times a week for 14-15 weeks with JPH 1701 (Ohmline) at 15 mg/kg in i.v. or with vehicle.

The growth of primary tumors was weekly evaluated by caliper measurement and by bioluminescence imaging (BLI). The tumor volume was calculated as length×width×depth and the primary tumor was surgical removed when its volume attempted 500 mm3 (6-7 weeks post graft). Mice were euthanized 8 weeks after tumor excision and metastases were detected ex vivo by bioluminescence imaging in lymph nodes, lungs, rachis, and bone legs.

A.9. Bioluminescence Imaging (BLI)

All of the mice were assessed weekly using whole-body bioluminescent imaging to quantify relative amounts of metastasis burden (ΦImageur™; BIOSPACE Lab, France). Each mouse was given potassium salt of D-luciferin (Interchim) at dose of 150 mg/kg body weight by intraperitoneal injection and anesthetized with Ketamin/xylasin i.p. injection. Bioluminescent images were collected in real time until saturation plate was reached in the lateral, ventral and dorsal positions. The levels of light emitted from the bioluminescent tumor cells were detected by the photon imager system, integrated, digitized, and displayed. Regions of interest were drawn around the experimental metastases. The amount of metastasis burden within each region of interest was quantified as the relative amount of light produced from the luciferase activity in breast cancer cells and expressed in cpm using the Photovision+ software (version 1.3; Biospace Lab). At necropsy, ex vivo BLI measurement were performed for each tissues collected.

B. Results

B.1. Identification of Alkyl Lipids as New Blockers of SK3/KCa2.3 Channel and Thereby Inhibitors of Cell Motility We have demonstrated that a small-conductance $Ca^{2+}$-activated K+ channels family, SK3 or KCa2.3 channel, is a mediator of epithelial cancer and melanoma cell motility (Potier et al., Mol Cancer Ther. 2006 November; 5(11):2946-53; Chantome et al., Exp Cell Res. 2009 Dec. 10; 315(20): 3620-30). Recently, the role of this channel on metastasis was demonstrated and we found that this channel promotes metastasis development (WO2008015267, <<A method for the in vitro screening of anti-cancer compounds that inhibits SK3/KCa2.3, and said anti-cancer compounds>>). Using this patent (WO2008015267), we screened compounds on their ability to decrease migration mediates by SK3/KCa2.3 channel of MDA-MB-435s cells. We found that edelfosine decrease the migration mediates by SK3/KCa2.3 channel (Potier et al., Br J Pharmacol. 2011 162(2), 464-79). Therefore, we decided to focus the screening on alkyl-lipids molecules and particularly on those that have a structure close to edelfosine. Edelfosine is an ether lipid, also known as an anti-tumour agent. This compound is however highly toxic when administered to human. Chemotherapeutic activity of ether lipids is believed in the art to arise, at least in part, from their ability to accumulate in cancer cells, due to the lack in these cells of the alkyl cleavage enzymes necessary for hydrolysis, and hence, removal of these lipids. It is believed in the art that exertion of detergent-like activity by ether lipids collected in cancer cell membranes can disturb the structure of the membranes, and hence, disrupt the cells. In this context, it is believed that the anti-cancer effect of edelfosine is mediated by the presence of the phosphocholine moiety (Mollinedo et al., 1997, Cancer Research, Vol. 57(7: 1320-1328); Mollinedo et al., 2004, Curr Med Chem, Vol. 11(24: 3163-3184).

Our aim was to design a "true" anti-metastatic drug that would specifically target intracellular pathway related to the migration of metastatic cells. Indeed, non-specific treatment often causes severe side effects (e.g., immune suppression, pancytopenia (anaemia, thrombocytopenia, and bone marrow cell growth inhibition accompanied by leucopenia), diarrhea, vomiting, and epilation (hair reduction)).

We therefore chose to test different alkyl-lipid analogues based on their structure in the hope to identify which parts of the compound are essential for its inhibitory activity on cell migration. Then, we test molecules in which the glycerol backbone was removed or in which sn-1, sn-2 or sn-3 were removed or replaced. The activity of the different compounds tested was summarized in table 2. We found that the glycerol backbone is essential because in its absence the analogues were more toxic and ineffective on cell migration (see analogues 2, 3, table 2). The length of the fatty chain in sn-1 position is crucial as shorter chains analogues are also ineffective in cell migration (see analogue 6, table 2). Same conclusion with the presence of an ether bond in sn-1 (see analogue 8, table 2). Then we tested compounds in which the sn-2 part was modified and found that analogues like PAF (compound 4) have no effect on cell migration. Finally, we found that the parts on sn-3 are essential (analogues 9-17). Indeed, removing the phosphocholine on sn-3 decrease its inhibitory effect on cell migration (compound 10). Interestingly, when we further added monosaccharide on sn-3 (analogues 11-15) the inhibitory activity reappears. The analogue was even more effective when a disaccharide is added (see analogue 17 and table 2).

In conclusion we identify that the ether bond in sn-1, a fatty chain length of at least 16 carbons in sn-1, an O—CH3 part in sn3 and a component like a phosphocholine or a mono-disaccharide are essential for the inhibitory activity on cell migration. From this screening we focused our study on the JPH1701 that have C16 chain on sn-1 with an ether bond, an O—CH3 on sn-2 and a β-lactose on sn-3.

Figure 6A:
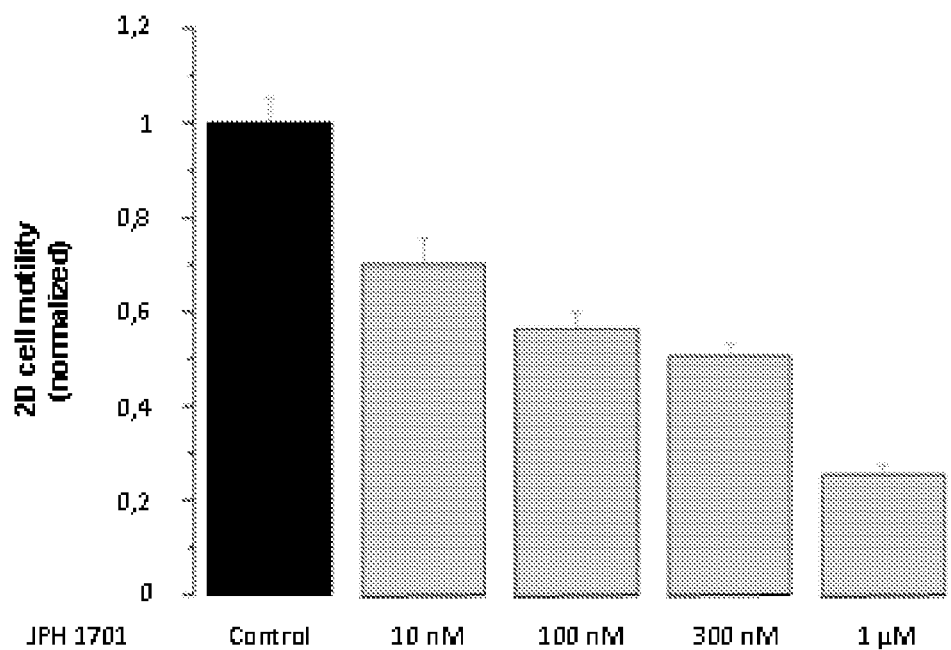
FIG. 6A-B) JPH1701 (the concentrations of JPH1701, for the FIG. 6A, are 0 (control condition), 10 nM, 100 nM, 300 nM and 1 µM) reduces motility (FIG. 6A) of MDA-MB-435s wild type (WT) cells from 10 nM without affecting viability (FIG. 6B) except at 10 µM.
Figure 6B:
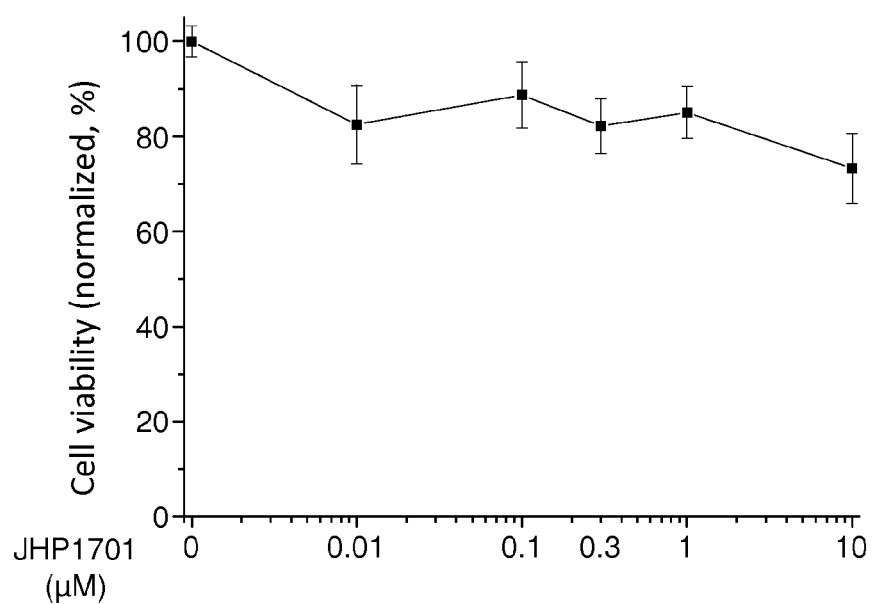
Figure 6C:
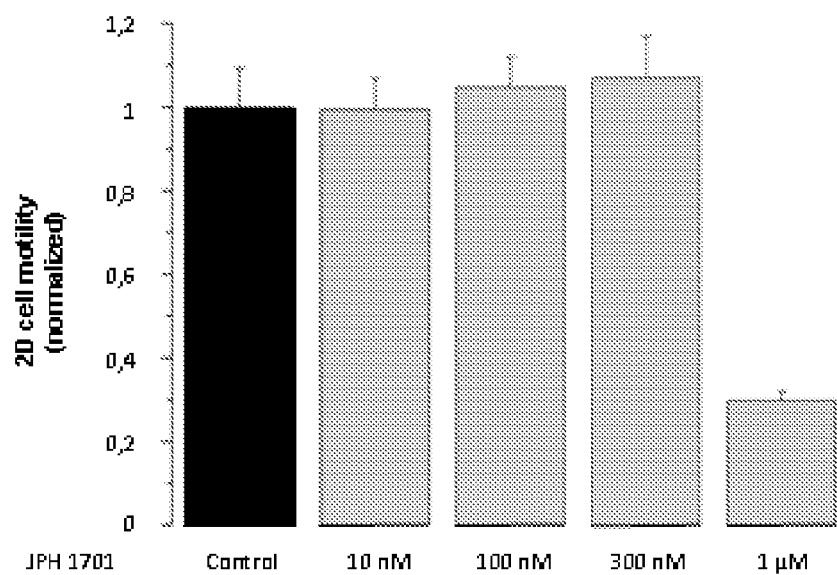
FIG. 6C-D) MCF-10A motility (FIG. 6C) and viability (FIG. 6D) are not affected by JPH1701 (the concentrations of JPH1701, for the FIG. 6C, are 0 (control condition), 10 nM, 100 nM, 300 nM and 1 µM).
Figure 6D:
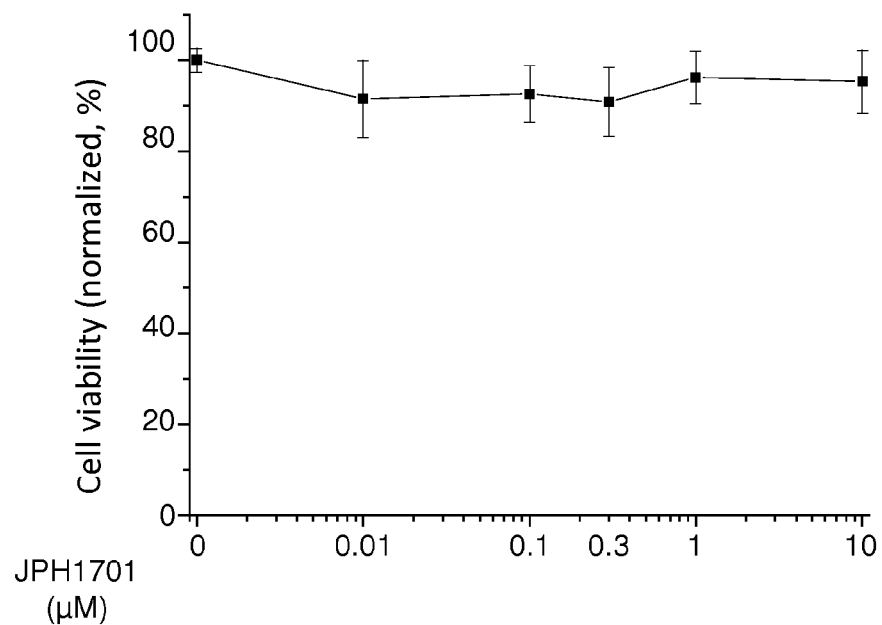
Figure 6E:
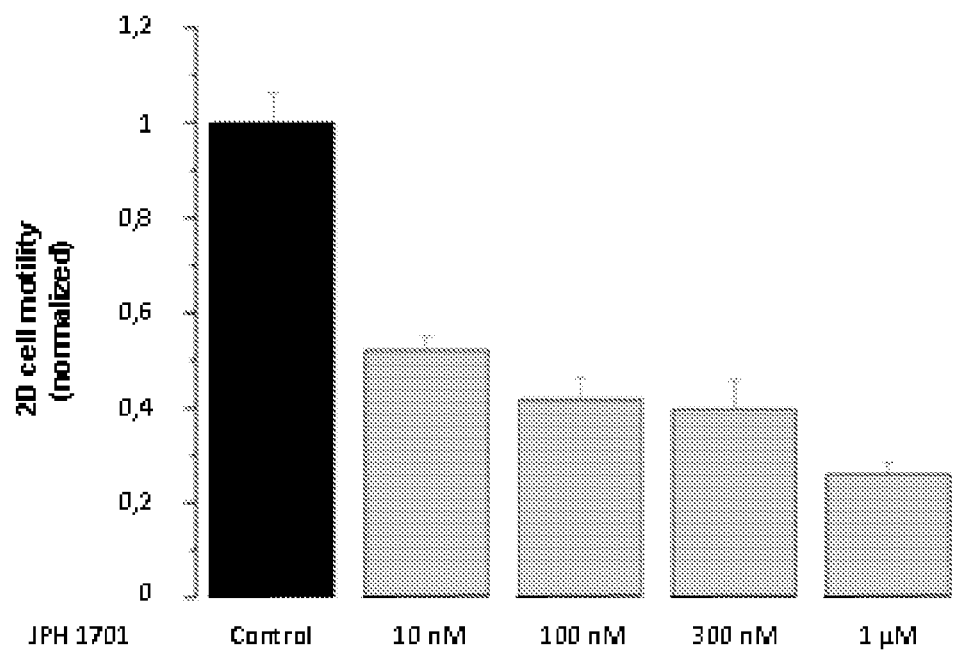
FIG. 6E-F) Effect on SK3 dependent motility.
Figure 6F:
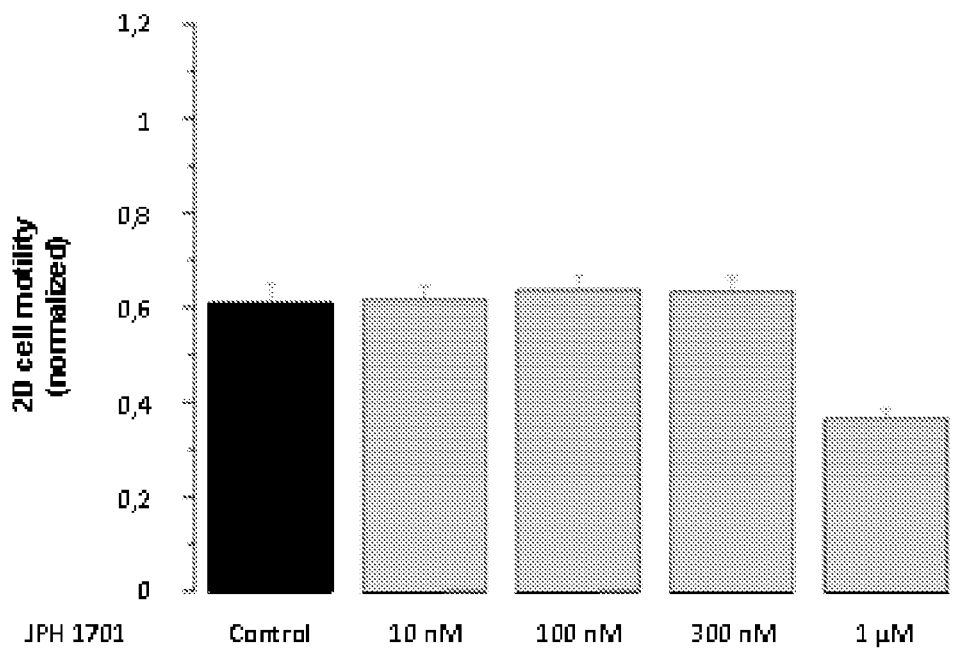

FIG. 6. shows that this analogue inhibits cell migration as from 10 nM with a maximal effect found around 1 μM (FIG. 6A). At these concentrations JPH1701 has no effect on cell viability (FIG. 6B). JPH1701 did not affected cell migration or the cell viability of non-cancerous cell MCF-10A (FIGS. 6C and 6D). FIG. 6E demonstrated that JPH1701 affect specially the SK3-dependant motility using cells that are infected with lentivirus coding for a shRNA directed against SK3. In control condition, with a shRNA random, we showed the same inhibition effect of JPH1701 that with the wild type cells (FIG. 6E). Without the SK3/KCa2.3 channel, the base level of migration is decreased (60% versus control condition). JPH1701 has any additive effect except at 1 μM on SK3-cells (FIG. 5 or 6C) that suggest a non specific effect of JPH1701 as observed at 1 μM with MCF-10A. Then, JPH1701 reduced the SK3-dependent migration of MDA-MB-435s cells.

Figure 7A:
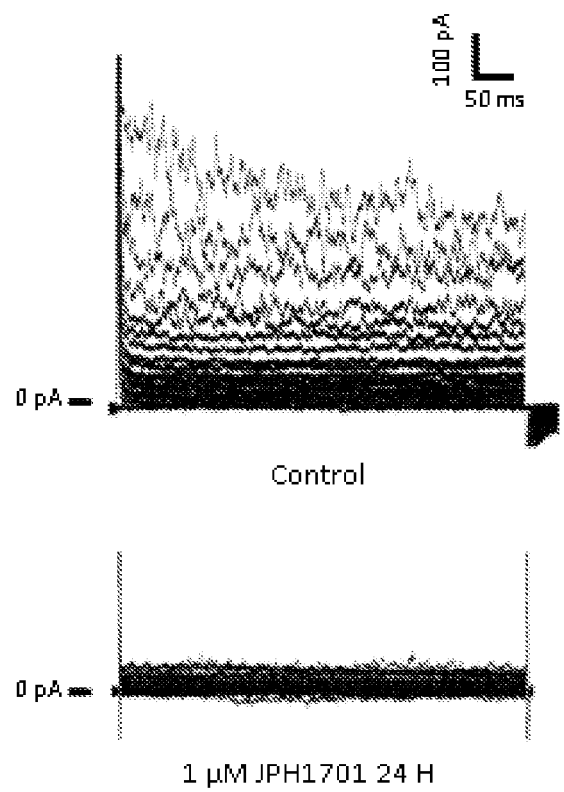
FIG. 7A) Illustrations of currents recorded on MDA-MD-435s. On the top, current were recorded on MDA-MB-435s in control condition. At the bottom, current were representative of a cell which was treated with JPH1701 1 µM during 24 hours.
Figure 7B:
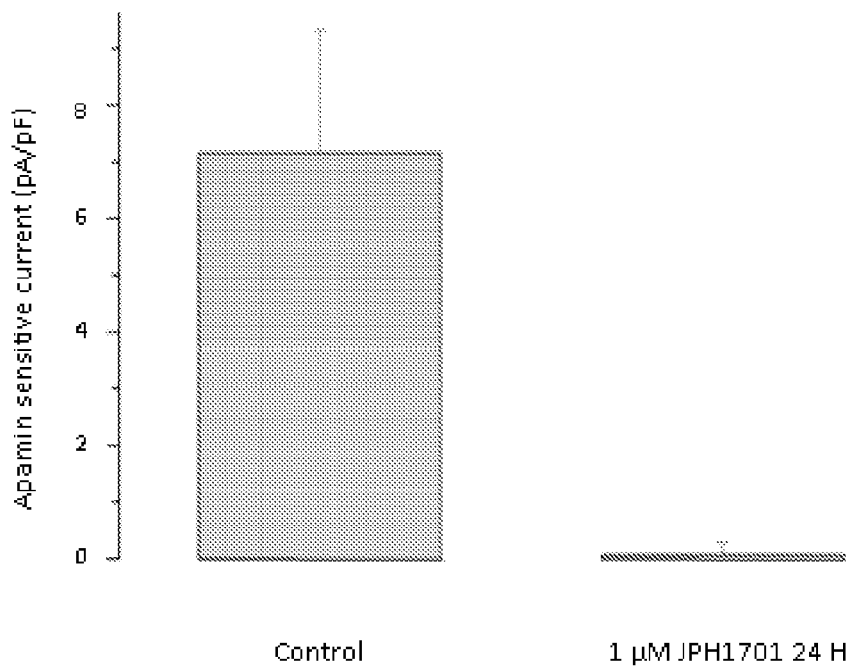
FIG. 7B) Effects of JPH1701 on apamin-sensitive currents. Cells were incubated with JHP1701 at 1 µM during 24 hours then currents were measured in absence or with apamin, a specific blocker of the SK3/KCa2.3 channel. Histograms show the amplitude of currents inhibited by apamin. After JPH1701 treatment apamin-sensitive current were abolished.

We next tested the effect of JPH1701 on the SK3 activity in MDA-MB-435s cells using patch clamp technique. These cells were treated for 24 h with 1 μM of JPH1701 before patch clamp assays. Compare to untreated cells, JPH1701 largely reduced SK3 currents (FIG. 7A). Indeed, the apamin-sensitive current was totally abolished after JPH1701 treatment (FIG. 7B).

We next developed HEK cells expressing SK3/KCa2.3 channel in order to test directly analogues on SK3 activity measured using patch-clamp technique (FIG. 8). We found that acute application of the molecule at 10 μM decreases SK3 current and that both the amplitude of the current recorded at 0 mV (current only carrying by SK3/KCa2.3 channel) and the SK3 conductance were decrease by JPH1701. The JPH1701-induced inhibition of SK3 current was analysed at 0 mV and the entire time course of the experiment is depicted in FIG. 8A. The effect of JPH1701 was dose dependent and whatever the concentration tested (300 nM, 1 μM, 10 μM), the entire inhibition was observed after 120 sec application. This inhibition was also time dependent. For example, 10 μM JPH1701 reduced by about 70% the amplitude of the current after 120 sec.

In addition, application of 10 nM apamin fully blocked the SK3 current (data not shown).

Figure 8A:
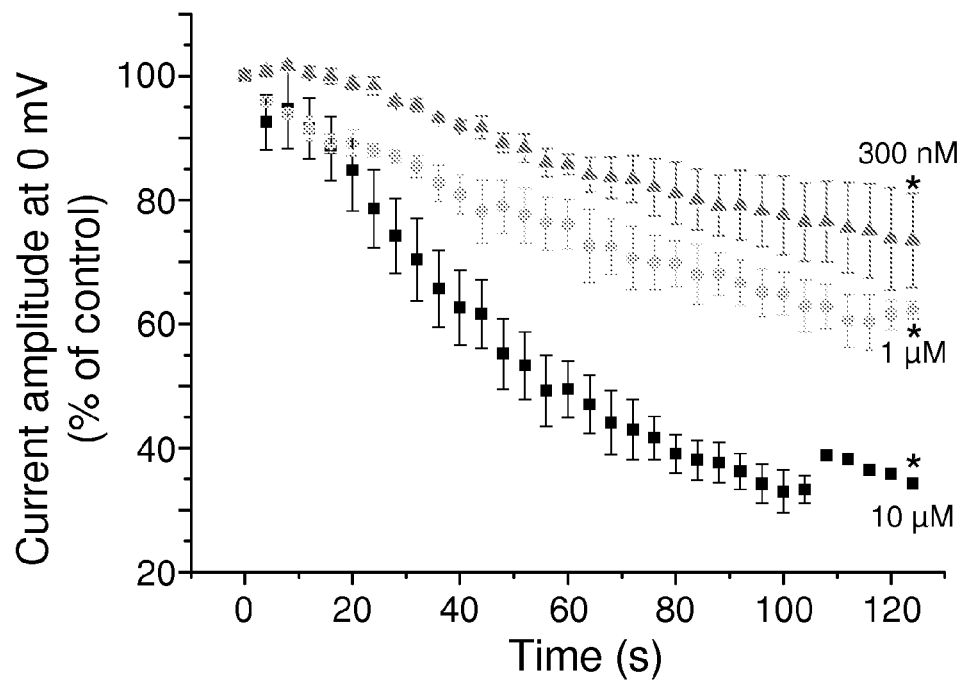
FIG. 8A) Dose and time responses effect of 3 different doses (300 nM, upper curve; 1 µM, middle curve and 10 µM bottom curve) of JPH1701 on SK3 current recorded at 0 mV. * means significantly different from control at p<0.05.
Figure 8B:
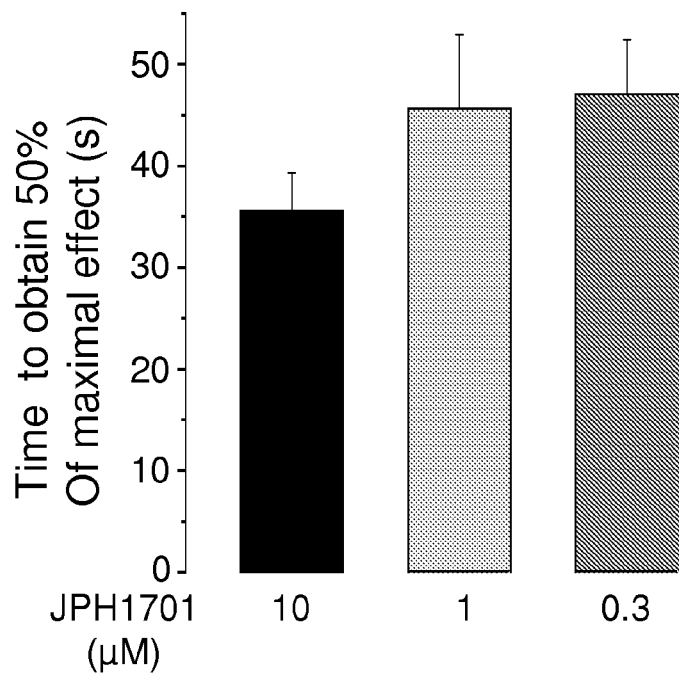
FIG. 8B) Histograms showing the dose independent effect of JPH1701 to obtain 50% of inhibition of the current (the concentrations of JPH 1701 are 10, 1 and 0.3 µM). Results are expressed as the mean±S.E.M.

We further analysed the time needed for JPH1701 for 0.3, 1 and 10 μM to obtain 50% of inhibition of the current (FIG. 8B). Whatever the concentration tested approximately 40 sec was needed to reduce 50% of the amplitude of the current. The endogenously HEK potassium current was not significantly affected by JPH1701 in the applied concentration range (data not shown). Increasing intracellular calcium concentration by the addition of 5 μM A23187 totally reversed the effect of JPH1701 (data not shown).

Figure 8C:
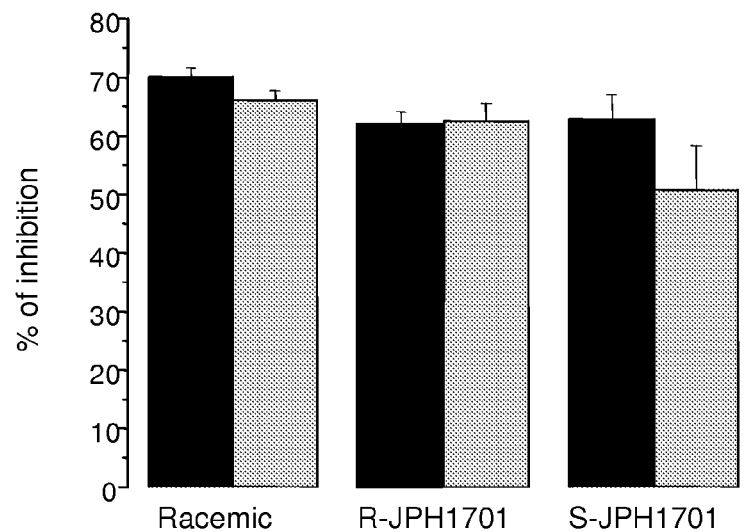
FIG. 8C) Histograms showing the effect of racemic hexadecyloxy-2-O-methyl-sn-glycerol-lactose (JPH 1701 or Ohmline, i.e: JPH1701 in the example) mixture and of both enantiomers (R-JPH1701 and S-JPH1701) on SK3 activity. The percentages of inhibition represent the ratio (SK3 current amplitude and chord conductance (in the presence of 10 µM JPH1701)/SK3 current amplitude in control experiments). Black bars show current at 0 mV and grey bars indicate the chord conductance.
Figure 8D:
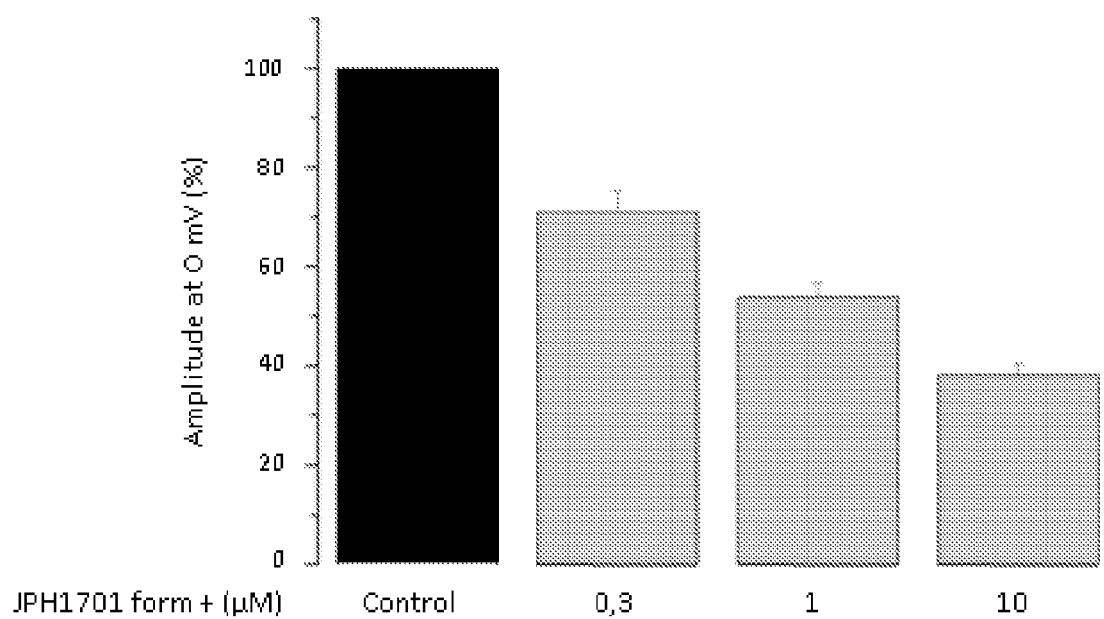
FIG. 8D) Dose-response effect of the form + of JPH1701 (concentrations: 0 (control), 0.3, 1 and 10 µM). Columns, mean, bars, SEM, (5 cells for racemic mix and 4 cells for + and − forms).

Since JPH1701 was tested as a racemic mixture, we asked if its capacity to reduce SK3 channel was specifically due to one of its enantiomers ((R-JPH1701 and (S)-JPH1701). The synthesis of the enantiomerically pure R- and S-JPH1701 was achieved from the enantiomerically pure (2R) and (2S) 1-O-hexadecyloxy-2-O-methyl-sn-glycerol. Compared to the racemic mixture, both enantiomers showed a similar behaviour in the reduction of SK3 channel activity (FIG. 8C). Thus, the following experiments were performed using an JPH1701 combination of both enantiomers.

To investigate whether JPH1701 interacts with the apamin binding site, 125I-apamin binding studies were performed.

Figure 8E:
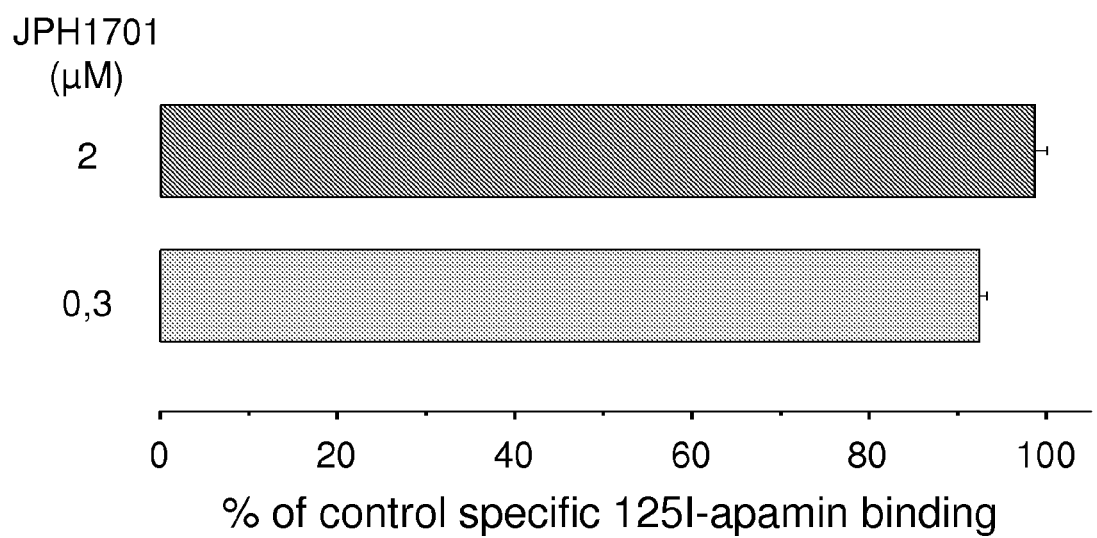
FIG. 8E) Histogram showing the % of control specific binding of $^{125}$I-Apamin (7 µM) to SKCa channel obtained from membrane homogenates of cerebral cortex by 0.3 and 2 µM JPH1701.

FIG. 8E shows that JPH1701 does not inhibit 125I-apamin binding to membrane expressing SKCa channels, suggesting that JPH1701 and apamin act through distinct site and mechanism that remain to be investigated.

Figure 9A:
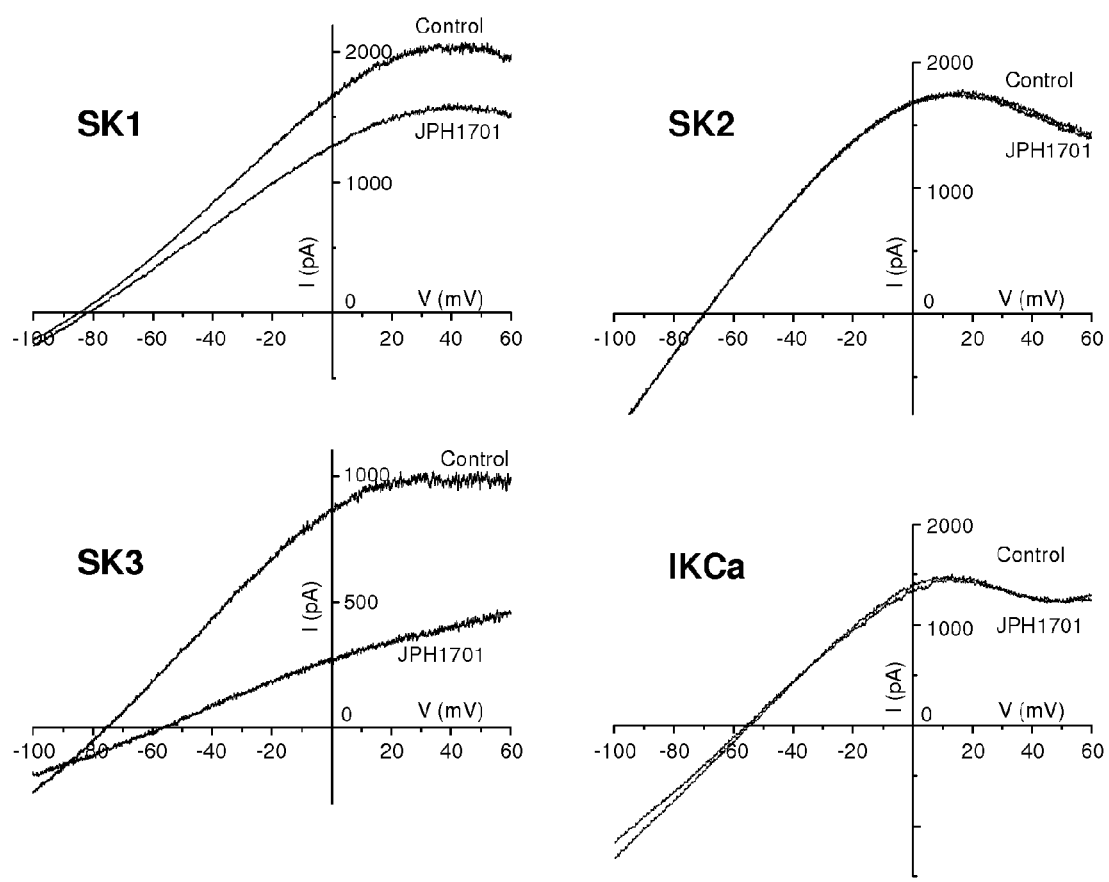
FIG. 9A) Example of whole-cell K$^+$ currents recorded in HEK293 cells expressing recombinants SK1, SK2, SK3 and IKCa channels before and after application of 10 µM JPH1701 (upper graphs: SK1 and SK2 respectively, bottom graphs: SK3 and IKCa respectively). Currents were generated by ramp protocol from −100 mV to +60 mV in 500 ms from a constant holding of 0 mV and with a pCa 6.
Figure 9B:
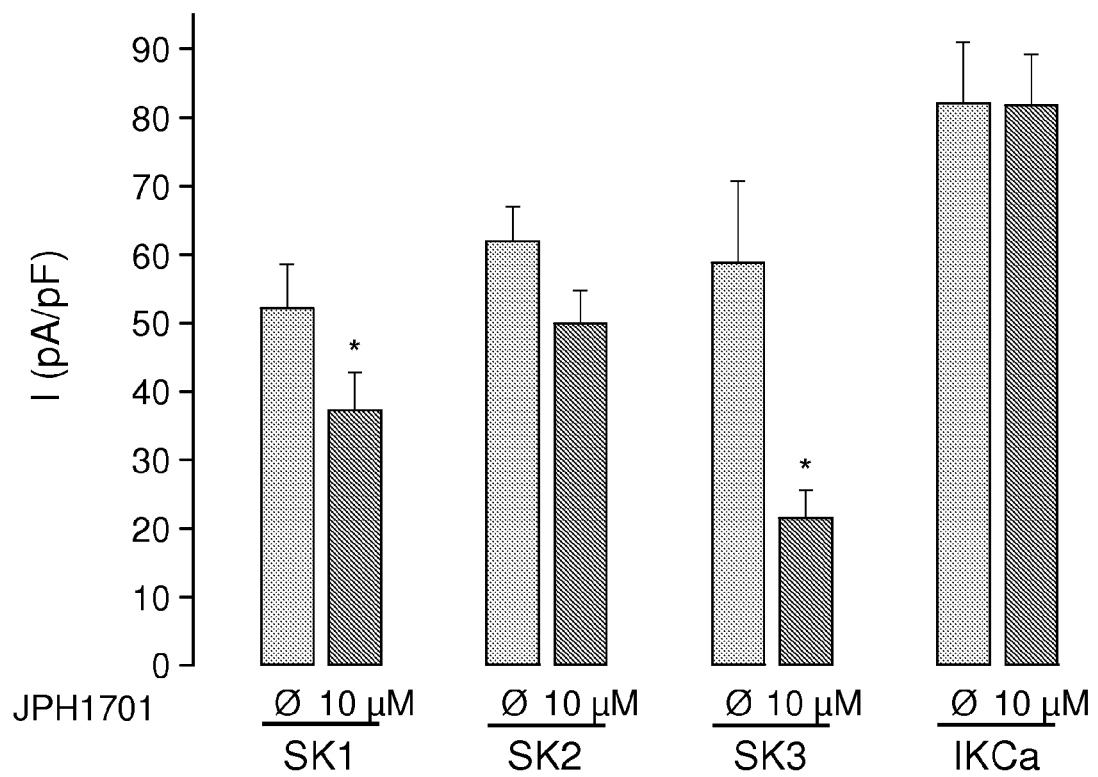
FIG. 9B) Histograms showing the effect of 10 µM JPH1701 on SKCa (SK1, SK2, SK3) and IKCa current amplitudes recorded at 0 mV. Results are expressed as the mean±S.E.M. * means significantly different from control at p<0.05. For each channel (SK1, SK2, SK3 and IKCa) the left column (pale grey) represents the control result and the right column (dark grey) represents the result after JPH1701 application.

The selectivity of JPH1701 toward the others members of the SKCa/IKCa channels was tested. FIG. 9A shows a representative whole-cell currents performed on SK1, SK2, SK3 and IKCa channels expressed in HEK cells in control condition and after application of 10 µM JPH1701. The experimental protocol was similar to the one used in FIG. 8. JPH1701 was tested for membrane potential from +60 mV to −100 mV on 500 msec. When the steady state inhibition was reached, 10 nM apamin or 1 µM clotrimazole were applied respectively to completely inhibit residual SKCa and IKCa currents. FIG. 9B shows that JPH1701 is inactive on IKCa currents but is able to significantly reduced SK1 and SK3 currents with a ranking potency SK3>SK1. At the concentration tested our compound was inactive on SK2 channels.

These results demonstrate that compounds of formula (I) and in particular compounds of formula (I) selected from the group of compounds (A to P, see detailed description of the invention) could be used to discriminate between SK2 and SK1/SK3 channel and would become useful tools to investigate the functional role of SK3 channel in peripheral tissues (that did not expressed SK1 channel).

In order to go further in the identification of analogues, melibiose or maltose hexadecyloxy-2-O-methyl-sn-glycerol (HMG) analogues were tested on SK3 current as well as JPH like molecules having O-acetyl on each carbon of lactose (Table 3). Melibiose and maltose both reduced SK3 activity, as well as JPH1700, which is a precursor of JPH1701 with groups O-acetyl on each carbon of lactose, but all these analogues has less effect.

Finally we tested the inhibitory effect on SK3 activity of compound where $R_3$ consists of:

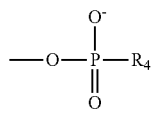

and wherein $R_4$ is selected from the group consisting of a monosaccharide group or a polysaccharide group having from 2 to 4 saccharide units (compounds M, N, O and P for example).

CHS31 (which is an example of compound M) is such an example of a hexadecyloxy-2-O-methyl-sn-glycerol analogue with a phosphate in its sn3 (i.e.: $R_3$) bond (see table 3). As JPH1700, this molecule reduced SK3 activity. Even if none of these compounds was as effective as JPH1701 this indicates that hexadecyloxy-2-O-methyl-sn-glycerol (HMG) disaccharide family has the potential to inhibit SK3 channel and therefore to present an anti-metastatic effect.

B.2. Anti-Metastatic Effect of JPH1701 on Experimental Metastasis Model

Recently we demonstrated that activity of SK3/KCa2.3 channel in cancer cell line MDA-MB-435s promotes metastasis development. To determine whether a SK3/KCa2.3 blocker such as JPH1701 could prevent metastasis development, we used a model of experimental metastasis with MDA-MB-435s cells expressing the firefly luciferase gene. Cancer cells were injected directly to the systemic circulation into the vein tail. One cohort of mice was treated with JPH1701 three times a week for 12 weeks by i.v. administration. Another cohort was treated with the vehicle in the same conditions. At the end of treatment, metastases were visualized in vivo by bioluminescence imaging (BLI) in 70% (7/10) of control mice and only in 40% (4/10) of JPH1701 treated-mice (Table 4). To go further, mice were sacrificed and detection of metastases in different tissues was performed ex vivo by BLI. The number of positive tissues from each cohort was show in Table 4. Metastatic lesions were detected in all vehicle-treated mice. Interestingly, 30% (3/10) of mice treated with JPH1701 showed no sign of metastasis development ex vivo. Using a clinical approach, we determined the metastatic profile of each mouse and found that JPH1701 treatment shifted the metastatic profile toward a less one (FIGS. 10A-B, 10C and 10D).

Figure 10A:
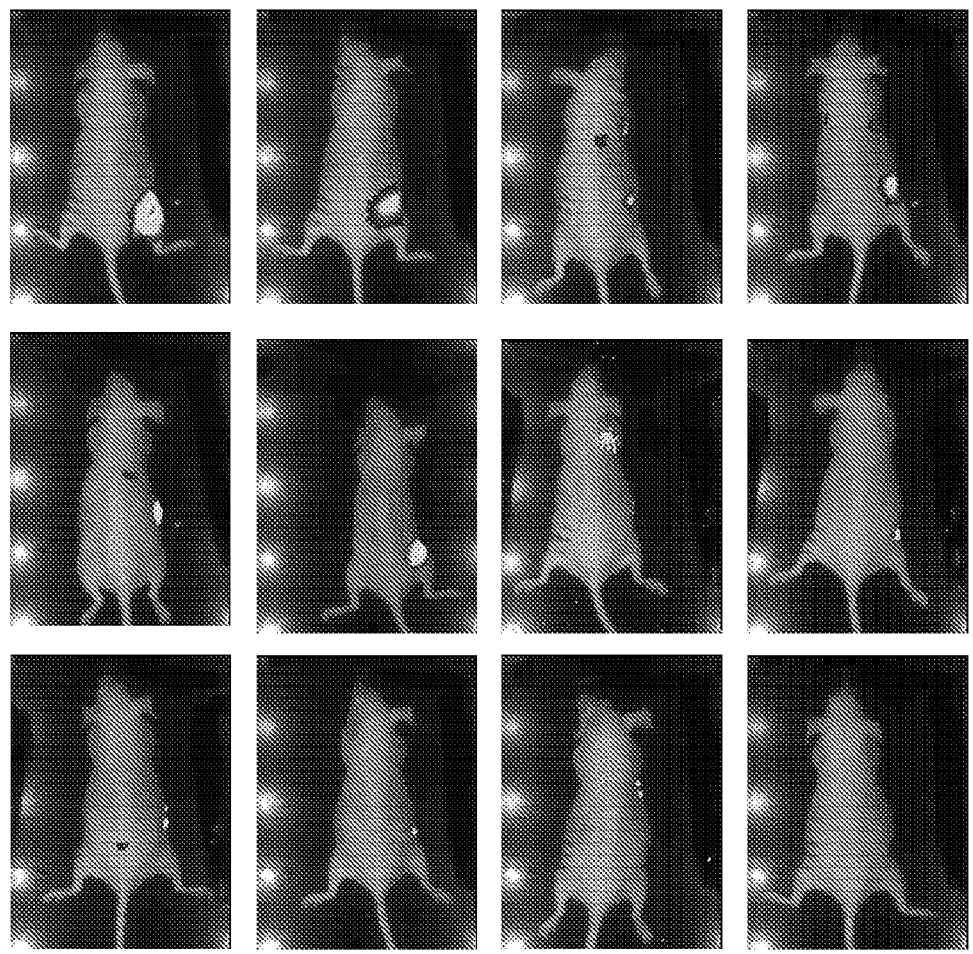
FIG. 10A-B) In vivo BLI of metastases from mice treated with vehicle (FIG. 10A) or with JPH1701 (FIG. 10B) before euthanasia.
Figure 10B:
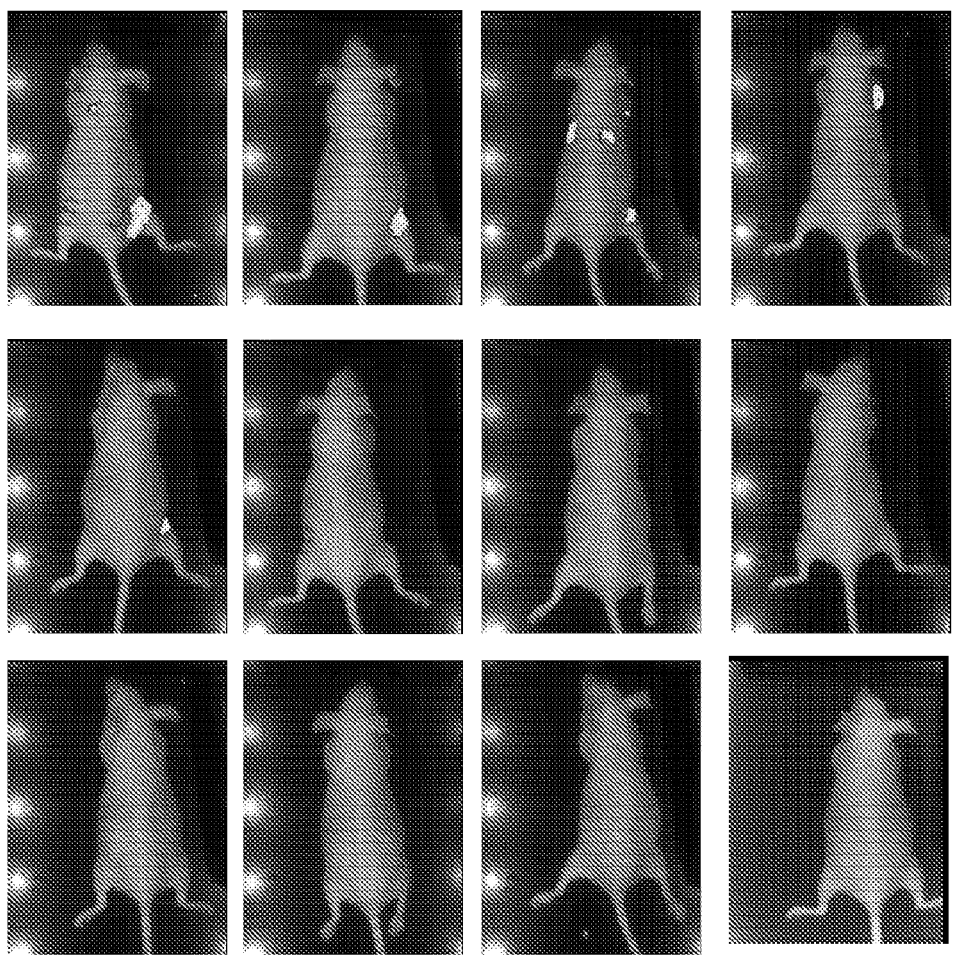
Figure 10C:
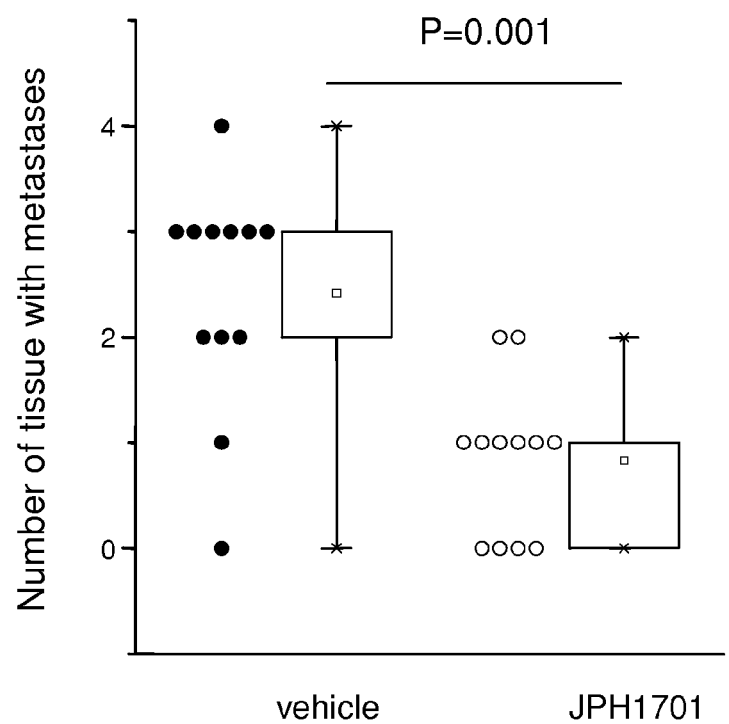
FIG. 10C) Number of tissue with metastases detected ex vivo by bioluminescence (including lymph nodes, lungs, rachis and bone legs) after euthanasia.
Figure 10D:
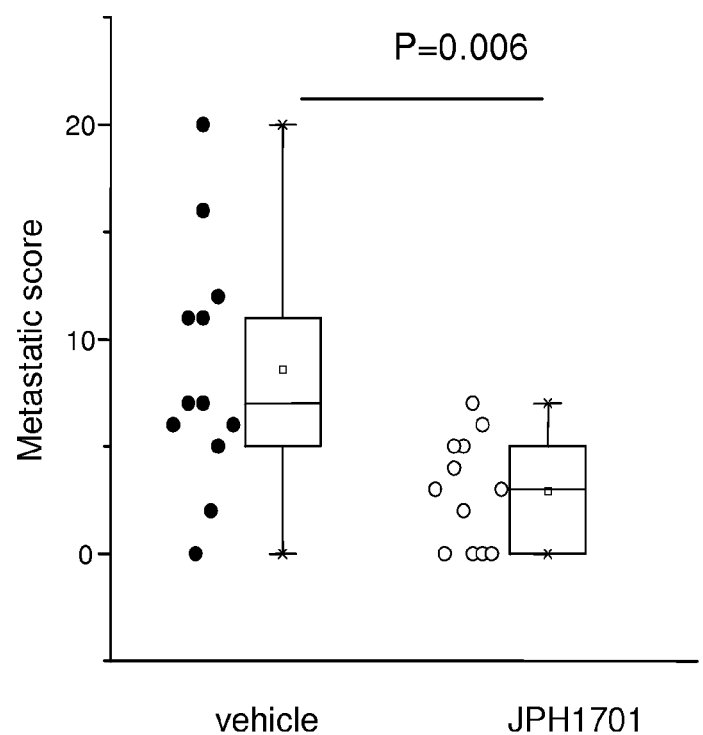
FIG. 10D) Metastatic score of mice treated with vehicle or with JPH1701. Two parameters were used to assess the metastatic score of each mouse: (i) Number of tissue or organ with metastases detected ex vivo by BLI and (ii) BLI intensity (photon/min) of each metastasis. Boxes indicated the first quartile, the median and the third quartile, squares indicated the mean. Statistical analysis, performed with Sigma stat software was made using Rank Sum Test. The difference between both cohorts of mice is significantly different.
Figure 10E:
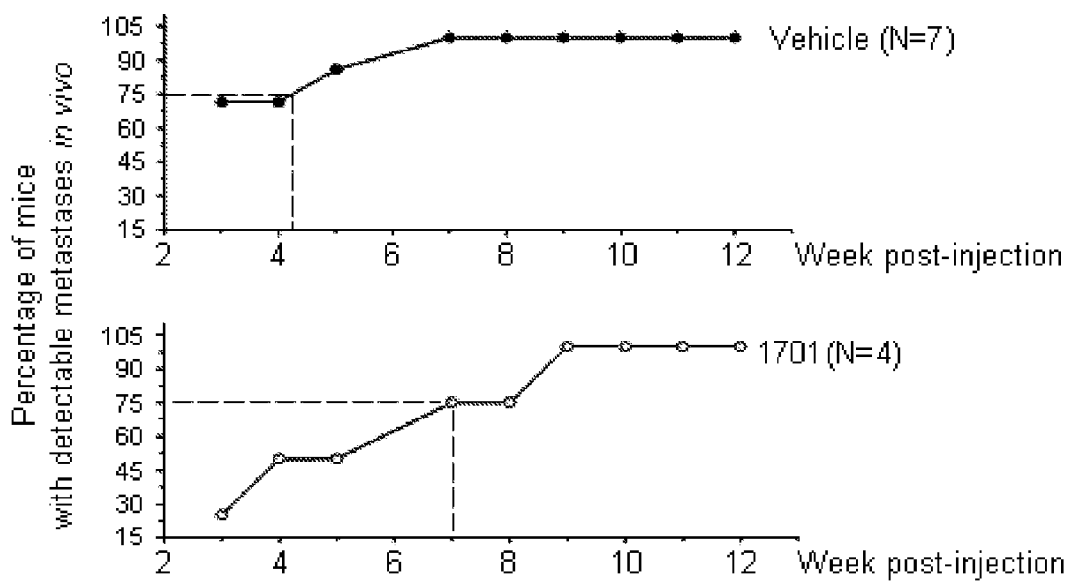
FIG. 10E) Percentage of mice showing metastases in vivo as a function of time. Data were normalized by designed the number of mice with metastases on week 12 (end point) as 100%. The upper panel depicts the results obtained in the control mice sub-group which have received a placebo composition (vehicle). The lower panel depicts the results obtained with mice which have received JPH1701. A comparison between the results depicted in the upper and lower panels shows that metastasis development was delayed or is lacking in JHP1701 treated-mice.
Figure 10F:
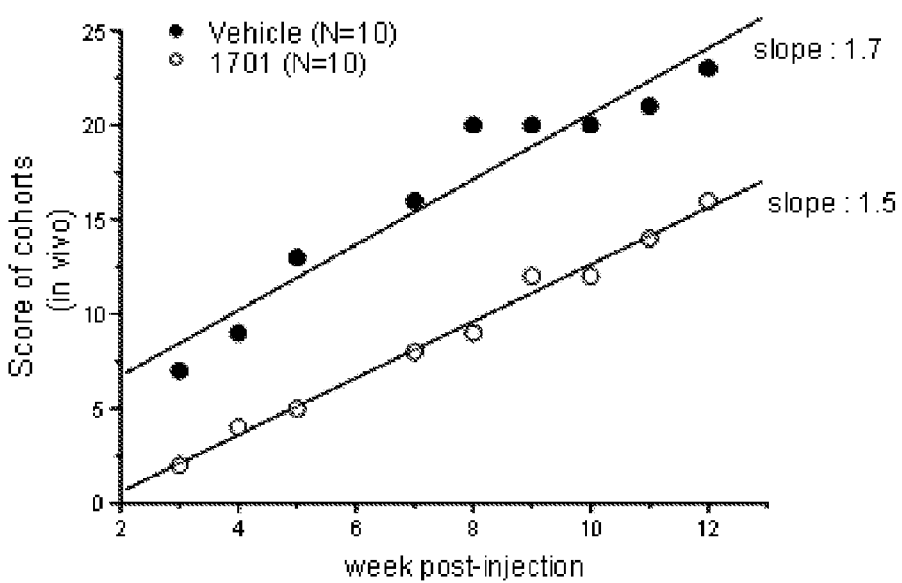
FIG. 10F) Graph representing the metastasis development in both cohorts: upper curve with filled circles: control mice sub-group which have received a placebo composition (vehicle); lower curve with empty circles: mice which have received JPH1701. The score of each cohort (sum of individually score) represents the degree of metastatic development assessed in vivo by BLI.

To obtain more information about anti-metastatic effect of JPH1701, we compared the kinetic of metastasis appearance between both cohorts by BLI. Only mice with metastases which are visualized in vivo on week 12 (end point) were included in this study. As shown in FIG. 10E, metastasis appearance was roughly 3 times faster in control group than in JPH1701 treated-group. Seventy five percent of mice treated with vehicle presented detectable metastases on week 4. Concerning JPH1701 treated-mice we need to wait 3 weeks more. In conclusion JPH1701 allowed the delay of metastasis formation in mice showing metastases in vivo (4/10). On the other hand, once metastases detected the growth rate was similar in both cohorts (FIG. 10F).

We have demonstrated in vitro that JPH1701 inhibited SK3-dependent motility but had no effect on MDA-MB-435s proliferation. In vivo data were coherent with these found in vitro: MDA-MB-435s were injected into the tail vein and they have to move toward pulmonary capillary vessels, of 10 µM diameter (as pore diameter in 2D motility assays), before to reach arterial blood on potential metastatic sites. JPH1701 impaired metastasis development probably by inhibiting SK3-dependent motility necessary for extra and intravasation of cancer cells. However, once cancer cells were reached a tissue with favourable environment for their proliferation, JPH1701 treatment did not prevent their proliferation.

B.3. JPH1701 Treatment does not Affect the Primary Tumor Growth

It has been also reported that edelfosine exerts its biological effect via several mechanisms and in particular through inhibition of enzyme activity like protein kinase C or phospholipase C. Those inhibitions may explain some of the cytostatic and cytotoxic effects of edelfosine (Gajate, C., and Mollinedo, F., Curr Drug Metab, 2002, 3, 491-525, Van Blitterswijk, W. J., and Verheij, M., Curr Pharm Des, 2008, 14, 2061-2074).

We demonstrated that JPH1701 was unable to interact with all PKCs and only slightly interact with PLC compare to edelfosine.

Figure 11A:
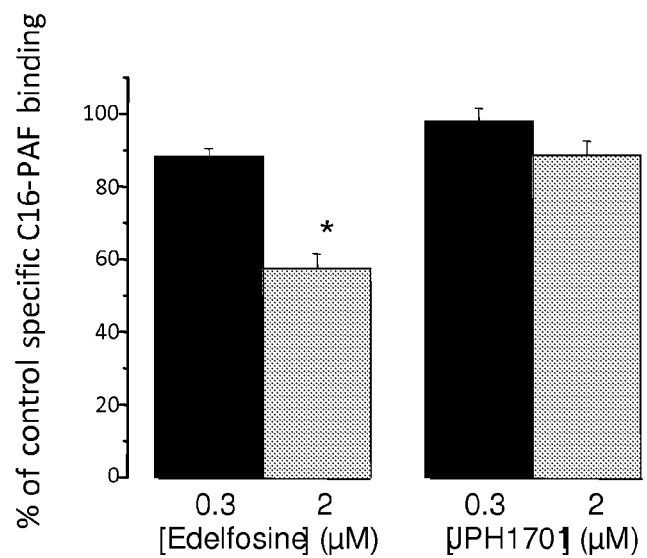
FIG. 11A) Histogram showing the percentage of control specific binding of 3H-C16-PAF to recombinant PAF receptor obtained from membrane homogenates of CHO cells by 0.3 and 2 µM edelfosine and by 0.3 and 2 µM JPH1701.
Figure 11B:
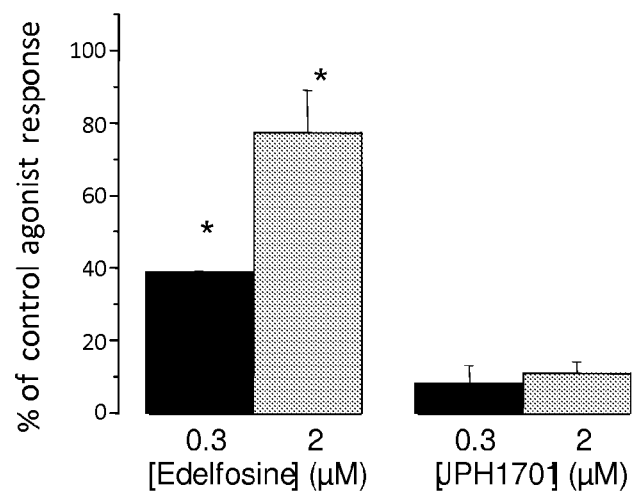
FIG. 11B) Histogram showing the percentage of control agonist response (% effect i.e: increase of intracellular calcium concentration) of 0.3 and 2 µM edelfosine and JPH1701 on PAF receptor normalized to the response induced by 100 nM C16-PAF. $IC_{50}$ were determined for edelfosine and JPH1701. * means significantly different from control at $p<0.05$.

Indeed, the molecular structure of JPH1701 resembles to LPA and PAF. This similarity between the molecular structures prompted us to analyse whether some of the JPH1701's effects were mediated through its binding to the PAF receptor or to the LPA (lysophosphatidic acid) receptor. As shown in FIG. 11 edelfosine was able to interact with C16-PAF binding site of PAF receptor (FIG. 11A) and therefore to dose-dependently increase intracellular calcium (FIG. 11B). In contrast JPH1701 was unable to interact with PAF receptor. The same results were obtained with LPA receptor (105.3±8.0% and 87.2±4.7% of LPA binding respectively at 0.3 and 2 µM JPH1701).

Figure 11C:
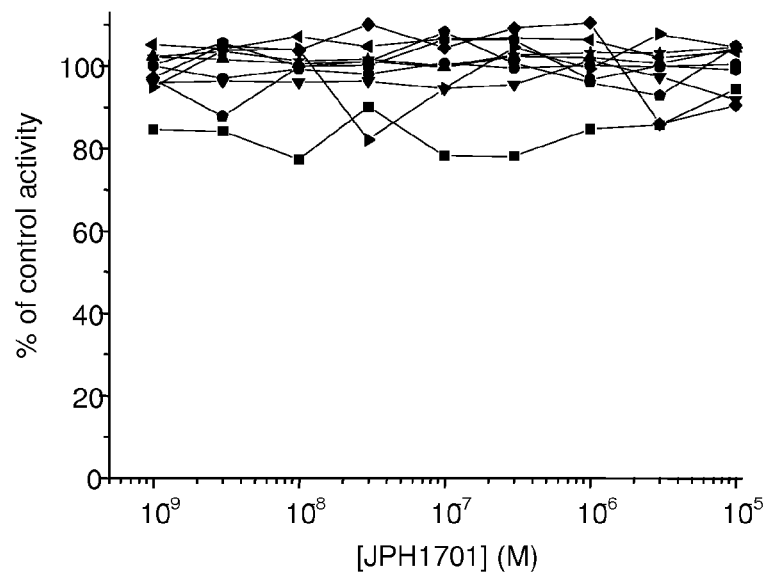
FIG. 11C-D) Dose responses curves showing the effect of JPH1701 on PKCs (FIG. 11C, PKCs are: alpha, Beta 1, Beta 2, Gamma, Delta, Epsilon, Zeta, Eta, Theta, Iota) and PhosphoLipase C (PLC) activities (FIG. 11D).
Figure 11D:
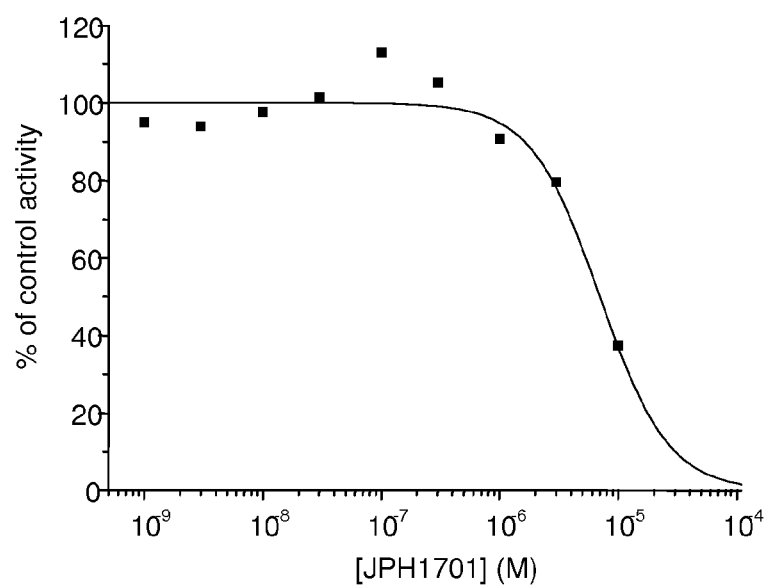

It has been also reported that edelfosine inhibits enzyme activity like protein kinase C or phospholipase C that may explain some of its cytostatic and cytotoxic effects. FIG. 11D shows that JPH1701 was able to interact with PLC activity with an $IC_{50}$ of 7.0 µM that is a much higher value than the one determines for edelfosine ($IC_{50}$ of 2.5 µM).
Regarding PKC activity, JPH1701 did not affect the activity of any of the ten PKCs family, (FIG. 11C)

Figure 12A:
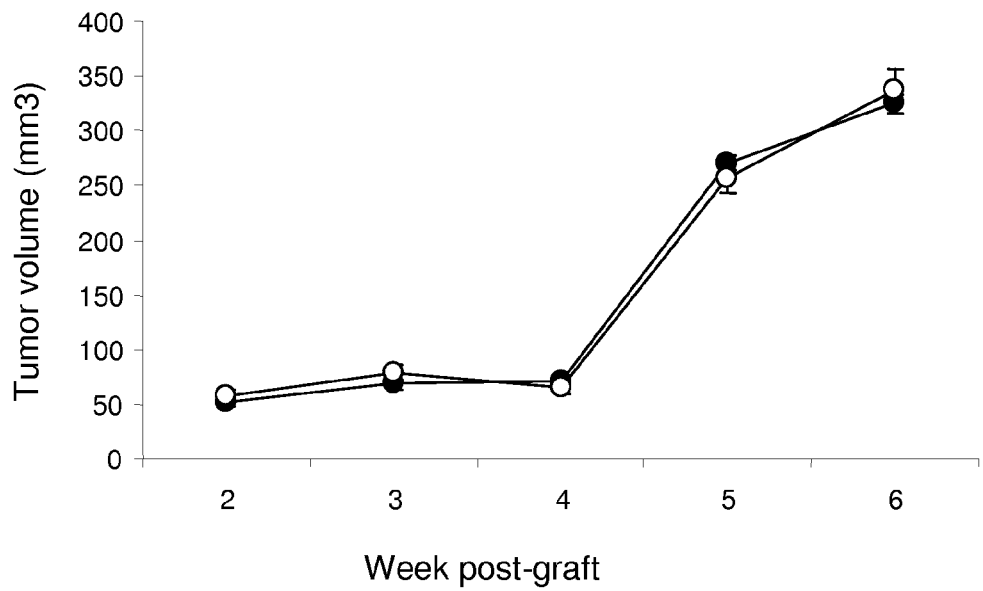
FIG. 12A) Time course of tumor volume. Two weeks post-graft, primary tumors were measured, weekly, during 6 weeks in three dimensions with a caliper and tumor volume was calculated (black circles: vehicle, open circles: JPH1701).
Figure 12B:
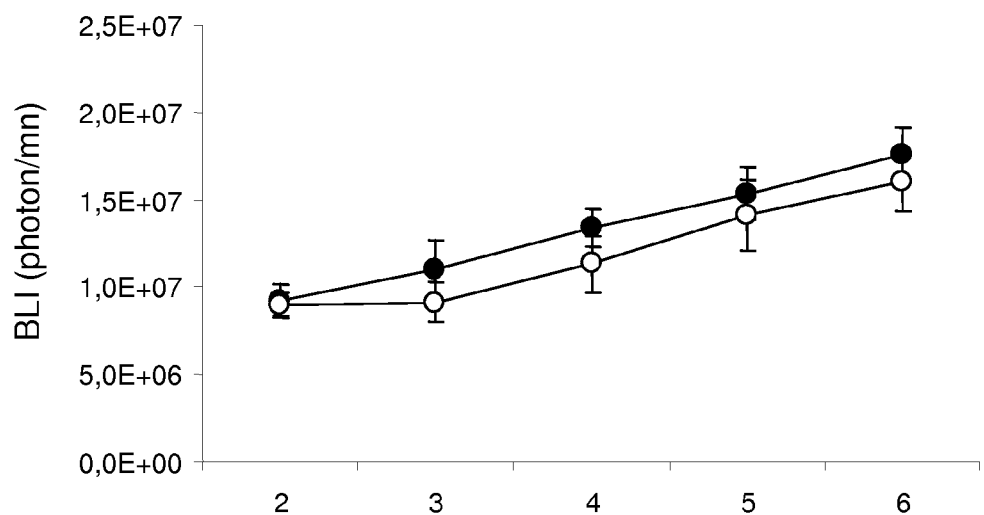
FIG. 12B) Time course of tumor BLI. Two weeks post-graft, the number of cancer cells in the primary tumor was evaluated weekly during 6 weeks by BLI imaging (black circles: vehicle, open circles: JPH1701). No difference was observed between the control cohort and the cohort of mice treated with JPH1701.

Lastly, we demonstrated that unlike edelfosine, JPH1701 does not target the primary tumor growth and is therefore specific to metastatic processes. Two millions of MDA-MB-435s-luc cells pre-treated for 24 hours with JPH 1701 (Ohmline) (1 µM) or vehicle were grafted in Mammary Fat Pad of NMRI/Nude mice. Mice were treated three times a week with JPH1701 at 15 mg/kg in i.v. or with vehicle. When looking at the time course of tumor volume over 6 weeks after the graft, there was no difference between vehicle and JPH1701 treated mice (FIG. 12A). Similarly, the weekly evaluation of the number of cancer cells in the primary tumor during 6 weeks did not highlighted any significant difference between vehicle and JPH1701 treated mice (FIG. 12B).

The limited effect of glycerolipid of formula (I) on cell viability of non cancerous epithelia cell compare to non specific compound such as edelfosine, associated with their action on SK3-cell migration at low concentrations, is promising because the pitfalls associated with the use of edelfosine like compounds have been that their effective and high concentrations are generally cytotoxic due to their detergent-like character causing normal cell lysis.

TABLE 1

| Compound of formula (I) | Cytotoxicity $IC_{50}$ (µM) | Cell Migration inhibition of MDA-MB-435s (SK3+) | |
|---|---|---|---|
| | | Inhibitory effect (%) | Concentration (nM) |
| 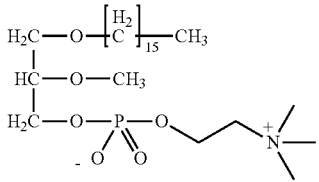 1321 | ±30 | 50 | 100 |
| 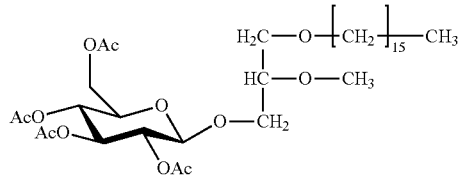 1518 | ±30 | 30 | 10 |
| 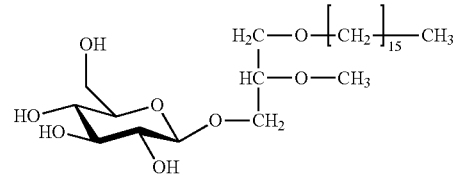 1523 | >10 | 50 | 300 |
| 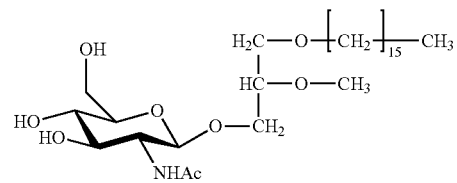 1528 | ±100 | 50 | 300 |
| 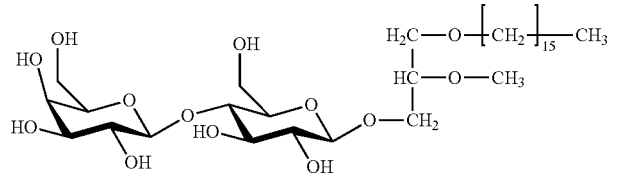 1701 | >10 | 50 | 300 |

TABLE 2

Molecules tested on the migration and of the viability of cancerous cell MDA-MB-435s

| N° | Molecules | Modifications | R1 | R2 | R3 |
|---|---|---|---|---|---|
| 1 | Edelfosine | | —O—(CH2)17—CH3 | —O—CH3 | Phosphocholine |
|   | Edelfosine | | —O—(CH2)17—CH3 | —O—CH3 | Phosphocholine |
| 2 | Miltefosine | No glycerol | H3C—(CH2)17-Phosphocholine | | |
| 3 | SK55 | No glycerol | H3C—(CH2)17-Phosphocholine | | |
| 4 | PAF | R2 | —O—(CH2)15—CH3 | —O—CO—CH3 | Phosphocholine |
| 5 | HCG450 | R1 (decrease of carbon number) and R2 and R3 [(OAc)4BetaGlu] | —O—(CH2)4—CH3 | —OH | —O—(OAc)4betaGlu |
| 6 | HCG451 | R1 (decrease of carbon number) and R2 and R3 [(OH)4BetaGlu] | —O—(CH2)4—CH3 | —OH | —O—(OH)4betaGlu |
| 7 | JPH 1321 | R1 (decrease of carbon number) | —O—(CH2)15—CH3 | —O—CH3 | Phosphocholine |
| 8 | JPH 1324 | R1 (decrease of carbon number) and no ether bond | —(CH2)15—CH3 | —O—CH3 | Phosphocholine |
| 9 | GS 1361 | R2 (OH) and R3 (OH) | —O—(CH2)15—CH3 | —OH | —OH |
| 10 | JPH 1597 | R3 (OH) | —O—(CH2)15—CH3 | —O—CH3 | —OH |
| 11 (A) | JPH 1518 | R3 [(OAc)4BetaGlu] | —O—(CH2)15—CH3 | —O—CH3 | —O—(OAc)4betaGlu |
| 12 (B) | JPH 1519 | R3 [(OAc)4BetaGal] | —O—(CH2)15—CH3 | —O—CH3 | —O—(OAc)4betaGal |
| 13 (A) | JPH 1523 | R3 [(OH)4BetaGlu] | —O—(CH2)15—CH3 | —O—CH3 | —O—(OH)4betaGlu |
| 14 | JPH 1524 | R3 [(OH)4BetaGal] | —O—(CH2)15—CH3 | —O—CH3 | —O—(OH)4betaGal |
| 15 (C) | JPH 1528 | R3 [NHAc(OH)3BetaGlu] | —O—(CH2)15—CH3 | —O—CH3 | —O—NHAc(OH)3betaGlu |
| 16 | JPH 1731 | R1 (C18), R3 [(OH)7BetaLactose] | —O—(CH2)17—CH3 | —O—CH3 | —O—(OH)7betaLactose |
| 17 (D) | JPH 1701 | R3 [(OH)7BetaLactose] | —O—(CH2)15—CH3 | —O—CH3 | —O—(OH)7betaLactose |

| N° | Toxicity | IC 50 (µM) | Migration (% of inhibition) | Concentration (nM) |
|---|---|---|---|---|
| 1 | Yes at 10 µM | ±5 | 60 | 10 |
|   | Yes at 10 µM | ±5 | 80 | 300 |
| 2 | | ±10 | 20 | 300 |
| 3 | | ±20 | ND | ND |
| 4 | No until 100 µM | ND | No effect | 300 |
| 5 | Yes at 10 µM | ±30 | ND | ND |
| 6 | No until 100 µM | ND | No effect | 300 |
| 7 | Yes at 10 µM | ±30 | 50 | 100 |
| 8 | Yes at 3 µM | ±5 | 50 | 300 |
| 9 | No at 10 µM | ND | 40 | 300 |
| 10 | No at 10 µM | ±50 | No effect | 300 |
| 11 (A) | No up to 30 µM | ND | 30 | 10 |
| 12 (B) | ND | ND | 20 | 100 |
| 13 (A) | No at 10 µM | ND | 50 | 300 |
| 14 | Yes at 10 µM | ±10 | 20 | 300 |
| 15 (C) | No at 10 µM | ≥100 | 50 | 300 |
| 16 | ND | ND | 30 | 100 |
| 17 (D) | No at 10 µM | ND | 50 | 300 |

TABLE 3

New SK3 inhibitors molecules.

| Molecules | Structure | Inhibition of I at 0 mV (%) | Conductance decreasing (%) | Apamin-sensitive current in MDA-MB-435s (pA/pF) |
|---|---|---|---|---|
| JPH1874 | sn-3: melibiose OAc | 44.0 ± 5.5 | 34.1 ± 6.8 | ND |
| JPH1880 | sn-3: maltose OAc | 44.7 ± 5.0 | 46.1 ± 6.1 | ND |
| JPH1882 (I) | sn-3: melibiose | 44.2 ± 5.1 | 36.1 ± 8.5 | 0.167 ± 0.085 |

TABLE 3-continued

New SK3 inhibitors molecules.

| Molecules | Structure | Inhibition of I at 0 mV (%) | Conductance decreasing (%) | Apamin-sensitive current in MDA-MB-435s (pA/pF) |
|---|---|---|---|---|
| JPH1700 | sn-3: β-lactose OAc | 22.8 ± 2.1 | 18.1 ± 2.3 | ND |
| CHS31 | sn-3: phospho-β-lactose OAc | 42.5 ± 8.2 | 38.9 ± 5.5 | ND |
| JPH1701 (D) | sn-3: β-lactose | 70.1 ± 1.4 | 66.1 ± 1.5 | 0.071 ± 0.215 |

Table 3 shows the effect of different molecules on SK3 activity in 2 models. Current activity has been measured in HEK 293 LvSK3 and in MDA-MB-435s cells. The percentages represent the inhibition of current and of conductance by compounds on SK3 channel in HEK 293 cells. The apamin-sensitive current shows the part of residual current which is abolished by apamin in MDA-MB-435s wild-type cells.

TABLE 4

|  | vehicle | JPH1701 |
|---|---|---|
| In vivo | 7 | 4 |
| ex vivo | 10 | 7 |
| ovary/uterus | 2 | 0 |
| kidney | 1 | 0 |
| liver | 3 | 0 |
| lung | 9 | 5 |
| leg | 7 | 3 |
| column | 5 | 2 |
| spleen | 1 | 0 |
| lymph node | 2 | 1 |

*Number of mice with experimental metastases detected in vivo and ex vivo by BLI.
**Number of tissues with metastases detected by BLI. N = 10 for each cohort.

The invention claimed is:

1. A method for inhibiting or treating cancer metastasis with no effect on primary tumor growth, comprising a step of administering to a patient in need thereof a glycerolipid is selected from the group consisting of the compounds (A)-(K) and (M)-(O) below:

Compound (A):

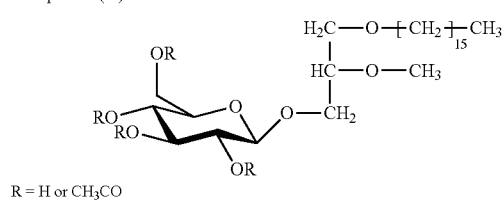

R = H or $CH_3CO$

Compound (B):

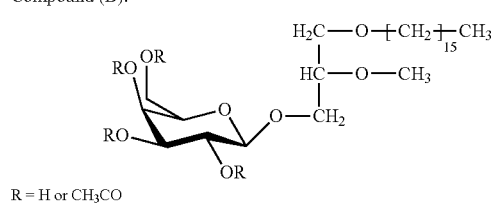

R = H or $CH_3CO$

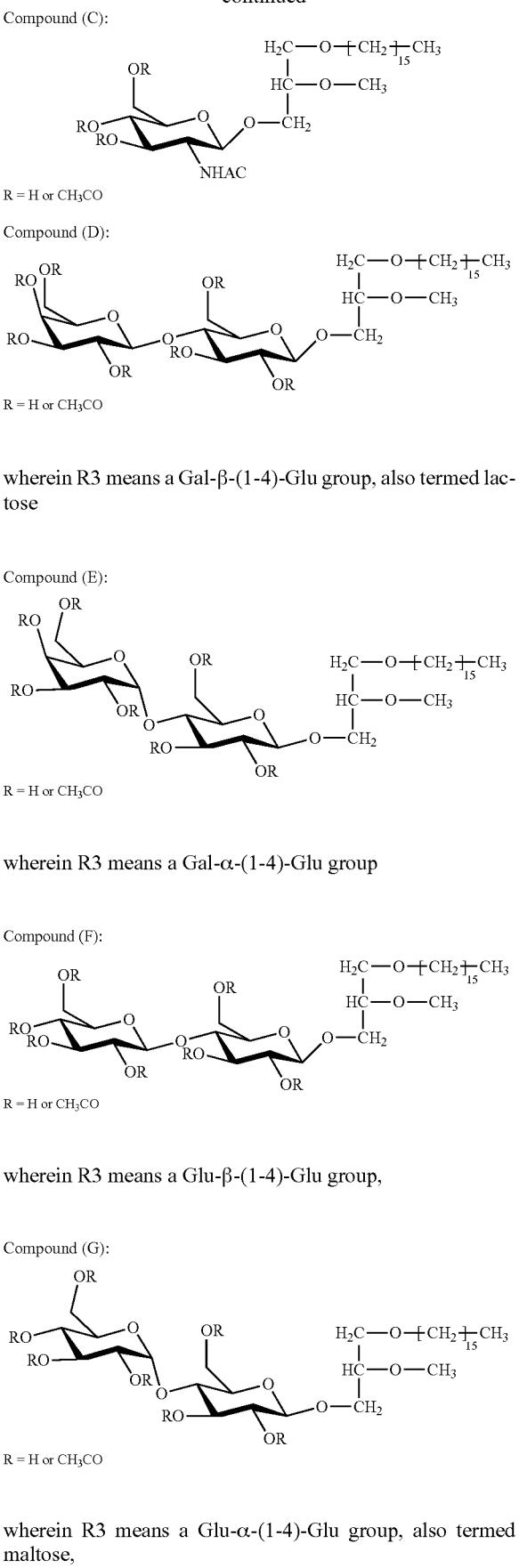

Compound (C):

R = H or $CH_3CO$

Compound (D):

R = H or $CH_3CO$ wherein R3 means a Gal-β-(1-4)-Glu group, also termed lactose

Compound (E):

R = H or $CH_3CO$ wherein R3 means a Gal-α-(1-4)-Glu group

Compound (F):

R = H or $CH_3CO$ wherein R3 means a Glu-β-(1-4)-Glu group,

Compound (G):

R = H or $CH_3CO$ wherein R3 means a Glu-α-(1-4)-Glu group, also termed maltose, Compound (H):

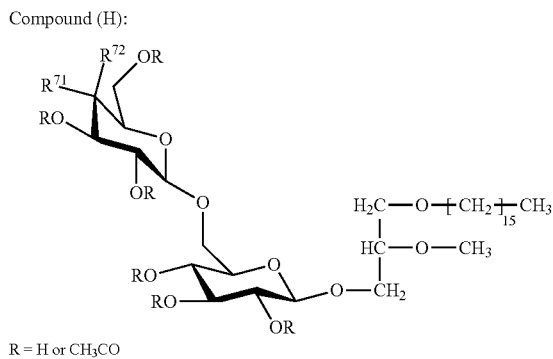

R = H or CH₃CO wherein $R^{71}$ and $R^{72}$ are independently selected from the group consisting of a hydrogen atom and a hydroxyl group or acetyl group, which encompasses (i) Gal-β-(1-6)-Glu when $R^{71}$ is H and $R^{72}$ is OH or OAcl and (ii) Glu-β-(1-6)-Glu when $R^{71}$ is OH or OAc and $R^{72}$ is H, Compound (I):

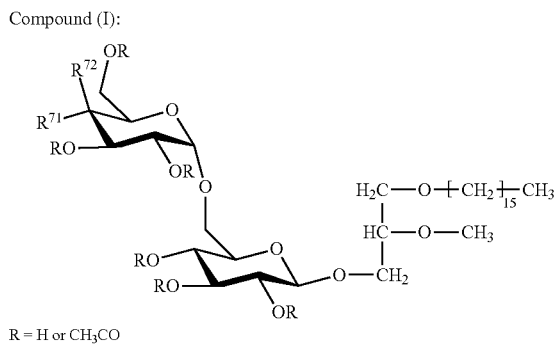

R = H or CH₃CO wherein $R^{71}$ and $R^{72}$ are independently selected from the group consisting of a hydrogen atom and a hydroxyl group or acetyl group, which encompasses (i) Gal-α-(1-6)-Glu when $R^{71}$ is H and $R^{72}$ is OH or OAc, also termed melibiose or acetylmelibiose and (ii) Glu-α-(1-6)-Glu when $R^{71}$ is OH or OAc and $R^{72}$ is H, Compound (J):

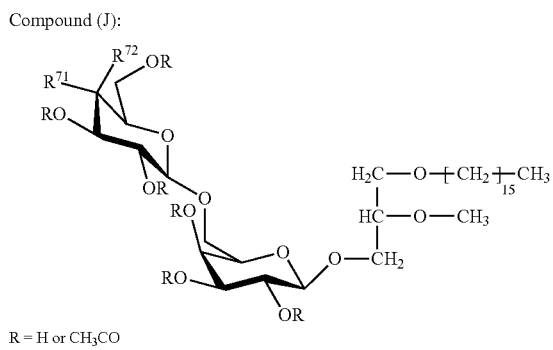

R = H or CH₃CO wherein $R^{71}$ and $R^{72}$ are independently selected from the group consisting of a hydrogen atom and a hydroxyl group or acetyl group, which encompasses (i) Gal-β-(1-6)-Gal when $R^{71}$ is H and $R^{72}$ is OH or OAc and (ii) Glu-β-(1-6)-Gal when $R^{71}$ is OH or OAc and $R^{72}$ is H Compound (K):

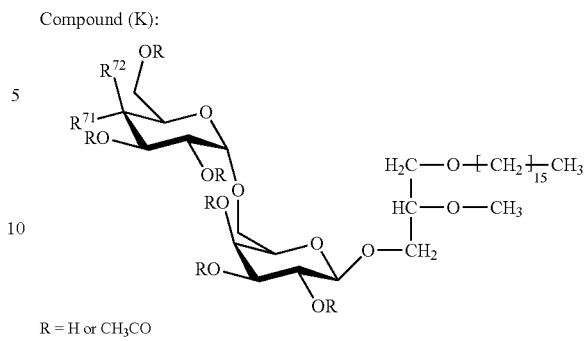

R = H or CH₃CO wherein $R_{71}$ and $R_{72}$ are independently selected from the group consisting of a hydrogen atom and a hydroxyl group or acetyl group, which encompasses (i) Gal-α-(1-6)-Gal when $R_{71}$ is H and $R_{72}$ is OH or OAc and (ii) Glu-α-(1-6)-Gal when $R_{71}$ is OH or OAc and $R_{72}$ is H, Compound (M):

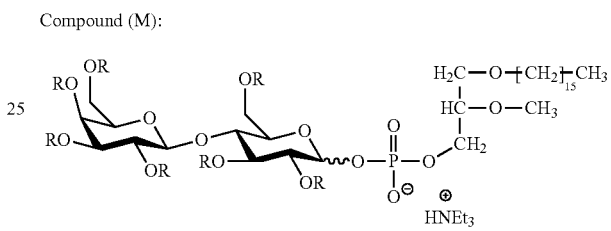

R = H or CH₃CO wherein $R_4$ means a Gal-β-(1-4)-Glu group, also termed lactose or acetyllactose, Compound (N):

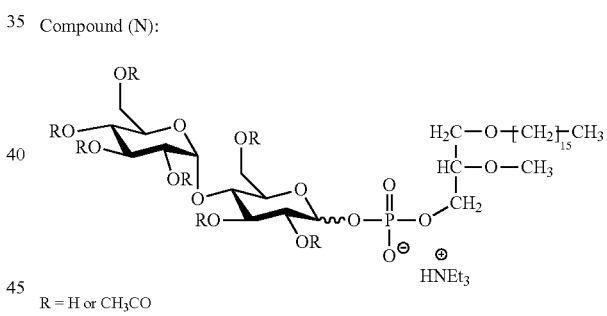

R = H or CH₃CO wherein $R_4$ means a Glu-α-(1-4)-Glu group, also termed maltose or acetylmaltose, Compound (O):

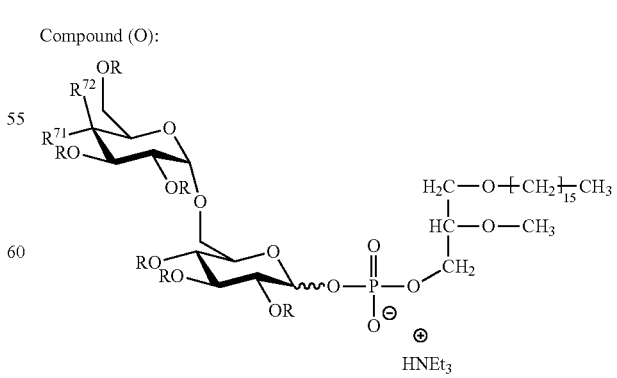

R = H or CH₃CO wherein $R^{71}$ and $R^{72}$ are independently selected from the group consisting of a hydrogen atom and a hydroxyl group or acetyl, which encompasses (i) Gal-α-(1-6)-Glu when $R^{71}$ is H and $R^{72}$ is OH or OAc, also termed melibiose or acetylmelibiose, and (ii) Glu-α-(1-6)-Glu when $R^{71}$ is OH or OAc and $R^{72}$ is H.

2. The method according to claim 1, wherein said method induces an inhibition of or blocks SK3/KCa2.3 channel activity.

3. The method according to claim 1, wherein said cancer is selected in the group consisting of apudoma, choristoma, branchioma, malignant carcinoid syndrome, carcinoid heart disease, carcinoma, histiocytic disorders, leukaemia, histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumours, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, cranio-pharyngioma, dysgerminoma, hamartoma, mesenchymoma, mesonephroma, myosarcoma, ameloblastoma, cementoma, odontoma, teratoma, thymoma, trophoblastic tumour, adenocarcinoma, adenoma, cholangioma, cholesteatoma, cylindroma, cystadenocarcinoma, cystadenoma, granulosa cell tumour, gynandroblastoma, hepatoma, hidradenoma, islet cell tumour, Leydig cell tumour, papilloma, Sertoli cell tumour, theca cell tumour, leiomyoma, leiomyosarcoma, myoblastoma, myoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, cystosarcoma phyllodes, leukosarcoma, ovarian carcinoma, sarcoma, neoplasms, neurofibromatosis and cervical dysplasia.

4. The method according to claim 1, wherein said method inhibits metastasis formation in tissues and organs selected in the group consisting of ovary, uterus, kidney, liver, lung, bone tissue, spleen, lymph nodes, colon, breast, brain, prostate and skin.

5. The method according to claim 1, wherein the amount of the glycerolipid that is administered at each dose is from 0.01 mg/kg to 100 mg/kg.

6. The method according to claim 1, wherein the glycerolipid is administered daily, bi-weekly, weekly, bi-monthly or monthly.

7. The method according to claim 1, wherein the glycerolipid is administered by a route selected in the group consisting of intradermal, intramuscular, intraperitoneal, intravenous, subcutaneous, intranasal, epidural and oral.

\* \* \* \* \*